US008323615B2

(12) United States Patent
Piran

(10) Patent No.: US 8,323,615 B2
(45) Date of Patent: Dec. 4, 2012

(54) METHODS OF PROCESSING MULTI-PHASIC DISPERSIONS

(75) Inventor: Uri Piran, Sharon, MA (US)

(73) Assignees: Baxter International Inc., Deerfield, IL (US); Baxter Healthcare S. A., Glattpark (Opfikon) (CH)

(*) Notice: Subject to any disclaimer, the term of this patent is extended or adjusted under 35 U.S.C. 154(b) by 891 days.

(21) Appl. No.: 12/195,149

(22) Filed: Aug. 20, 2008

(65) Prior Publication Data
US 2010/0047162 A1    Feb. 25, 2010

(51) Int. Cl.
A61K 51/00    (2006.01)
A61K 39/395    (2006.01)
A61K 39/00    (2006.01)
A61K 39/38    (2006.01)
A61K 39/385    (2006.01)
A61K 8/02    (2006.01)
A61K 9/14    (2006.01)
A61K 38/43    (2006.01)
A61K 38/00    (2006.01)
A61K 31/70    (2006.01)
A61K 48/00    (2006.01)
A01K 43/04    (2006.01)

(52) U.S. Cl. .......... 424/1.11; 424/130.1; 424/184.1; 424/193.1; 424/401; 424/486; 424/94.1; 514/1.1; 514/23; 514/44 R

(58) Field of Classification Search .......... 424/1.11, 424/130.1, 184.1, 193.1, 401, 486, 93.1; 514/1.1, 23, 44 R
See application file for complete search history.

(56) References Cited

U.S. PATENT DOCUMENTS

| | | |
|---|---|---|
| 3,737,337 A | 6/1973 | Schnoring at al. |
| 3,891,570 A | 6/1975 | Fukushima et al. |
| 4,389,330 A | 6/1983 | Tice et al. |
| 4,396,560 A | 8/1983 | Stofer |
| 4,416,859 A | 11/1983 | Brown et al. |
| 4,486,315 A | 12/1984 | Teipel |
| 4,530,840 A | 7/1985 | Tice et al. |
| 4,652,441 A | 3/1987 | Okada et al. |
| 4,728,721 A | 3/1988 | Yamamoto et al. |
| 4,732,333 A | 3/1988 | Aria |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum et al. |
| 4,917,893 A | 4/1990 | Okada et al. |
| 5,019,400 A | 5/1991 | Gombotz et al. |
| 5,075,109 A | 12/1991 | Tice et al. |
| 5,102,872 A | 4/1992 | Singh et al. |
| 5,149,543 A | 9/1992 | Cohen et al. |
| 5,160,745 A | 11/1992 | DeLuca et al. |
| 5,213,812 A | 5/1993 | Ruiz et al. |
| 5,227,239 A | 7/1993 | Upadhye et al. |
| 5,271,961 A | 12/1993 | Mathiowitz et al. |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,525,519 A | 6/1996 | Woiszwillo |
| 5,543,158 A | 8/1996 | Gref et al. |
| 5,554,730 A | 9/1996 | Woiszwillo et al. |
| 5,556,642 A | 9/1996 | Kobayashi et al. |
| 5,575,987 A | 11/1996 | Kamei et al. |
| 5,578,709 A | 11/1996 | Woiszwillo et al. |
| 5,599,719 A | 2/1997 | Woiszwillo et al. |
| 5,603,961 A | 2/1997 | Suzuki et al. |
| 5,620,883 A | 4/1997 | Shao et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,667,808 A | 9/1997 | Johnson et al. |
| 5,716,640 A | 2/1998 | Kamei et al. |

(Continued)

FOREIGN PATENT DOCUMENTS

DE    04312970    10/1994

(Continued)

OTHER PUBLICATIONS

Lossow et al. J. Lipid Research, 1969, 10, 68-76.*
Ashraf-Khorassani et al. Pharm. Dev. Technol. 2005, 10, 507-516.*
Ashraf-Khorassani et al. Pharmaceutical Development and Technology, 2005, 10, 507-516.*
Lossow et al. Journal of Lipid Research, 1969, 10, 68-76.*
Partial International Search Report from corresponding International Application No. PCT/US09/54525, dated Dec. 9, 2009.
Price, Centrifugation in Density Gradients, New York: Academic Press (1982). Table of Contents Only.
Ahn et al., "Biodegradable poly(ethylenimine) for plasmid DNA delivery," *J. Control. Rel.*, 80:273-282 (2002).
Al et al., "Nano-encapsulation of furosemide microcrystals for controlled drug release," *J. Control. Rel.*, 86:59-68 (2003).

(Continued)

*Primary Examiner* — Fereydoun G Sajjadi
*Assistant Examiner* — Genevieve S Alley
(74) *Attorney, Agent, or Firm* — Marshall, Gerstein & Borun LLP

(57) ABSTRACT

A method for processing multi-phasic dispersions is provided. The method comprises providing a multi-phasic dispersion, the dispersion including dispersed and continuous phases, the dispersion comprising solid microparticles, providing a non-solvent, combining the multi-phasic dispersion and the non-solvent, and selectively effecting migration of the dispersed phase into or through the non-solvent such that the microparticles are separated from the dispersion.

34 Claims, No Drawings

U.S. PATENT DOCUMENTS

| | | | |
|---|---|---|---|
| 5,851,451 A | 12/1998 | Takechi et al. |
| 5,891,478 A | 4/1999 | Johnson et al. |
| 5,932,248 A | 8/1999 | Chen et al. |
| 5,945,126 A | 8/1999 | Thanoo et al. |
| 5,972,707 A | 10/1999 | Roy et al. |
| 5,981,719 A | 11/1999 | Woiszwillo et al. |
| 5,989,463 A | 11/1999 | Tracy et al. |
| 6,020,175 A | 2/2000 | Onda et al. |
| 6,036,976 A | 3/2000 | Takechi et al. |
| 6,048,550 A | 4/2000 | Chan et al. |
| 6,051,259 A | 4/2000 | Johnson et al. |
| 6,063,910 A | 5/2000 | Debenedetti et al. |
| 6,090,925 A | 7/2000 | Woiszwillo et al. |
| 6,107,084 A | 8/2000 | Onda et al. |
| 6,113,795 A | 9/2000 | Subramaniam et al. |
| 6,120,787 A | 9/2000 | Gustafsson et al. |
| 6,140,475 A | 10/2000 | Margolin et al. |
| 6,153,211 A | 11/2000 | Hubbell et al. |
| 6,242,230 B1 | 6/2001 | Batich et al. |
| 6,265,389 B1 | 7/2001 | Burke |
| 6,268,053 B1 | 7/2001 | Woiszwillo et al. |
| 6,270,795 B1 | 8/2001 | Jones et al. |
| 6,270,802 B1 | 8/2001 | Thanoo et al. |
| 6,312,727 B1 | 11/2001 | Schacht et al. |
| 6,361,798 B1 | 3/2002 | Thanoo et al. |
| 6,395,253 B2 | 5/2002 | Levy et al. |
| 6,395,302 B1 | 5/2002 | Hennink et al. |
| 6,455,074 B1 | 9/2002 | Tracy et al. |
| RE37,872 E | 10/2002 | Franks et al. |
| 6,458,387 B1 | 10/2002 | Scott et al. |
| 6,467,630 B1 | 10/2002 | Zborowski et al. |
| 6,475,995 B1 | 11/2002 | Roy et al. |
| 6,479,146 B1 | 11/2002 | Caruso et al. |
| 6,500,107 B2 | 12/2002 | Brown et al. |
| 6,500,448 B1 | 12/2002 | Johnson et al. |
| 6,506,410 B1 | 1/2003 | Park et al. |
| 6,541,606 B2 | 4/2003 | Margolin et al. |
| 6,569,458 B1 | 5/2003 | Gombotz et al. |
| 6,596,316 B2 | 7/2003 | Lyons et al. |
| 6,616,949 B2 | 9/2003 | Jonsson et al. |
| 6,620,351 B2 | 9/2003 | Gupta et al. |
| RE38,385 E | 1/2004 | Franks et al. |
| 6,699,501 B1 | 3/2004 | Neu et al. |
| 6,713,533 B1 | 3/2004 | Panzner et al. |
| 6,749,866 B2 | 6/2004 | Bernstein et al. |
| 6,814,980 B2 | 11/2004 | Levy et al. |
| 6,830,737 B2 | 12/2004 | Ramstack |
| 6,833,192 B1 | 12/2004 | Caruso et al. |
| 6,861,064 B1 | 3/2005 | Laakso et al. |
| 6,998,051 B2 | 2/2006 | Chattopadhyay et al. |
| 7,374,782 B2 | 5/2008 | Brown et al. |
| 2001/0002261 A1 | 5/2001 | Morrison et al. |
| 2002/0137156 A1 | 9/2002 | Margolin et al. |
| 2002/0146459 A1 | 10/2002 | Levy et al. |
| 2002/0179540 A1 | 12/2002 | Perrut |
| 2002/0187197 A1 | 12/2002 | Caruso et al. |
| 2002/0197325 A1 | 12/2002 | Osborne |
| 2003/0007990 A1 | 1/2003 | Blankenship et al. |
| 2003/0026844 A1 | 2/2003 | Lee et al. |
| 2003/0059474 A1 | 3/2003 | Scott et al. |
| 2003/0064033 A1 | 4/2003 | Brown et al. |
| 2003/0075817 A1 | 4/2003 | Suzuki et al. |
| 2003/0124368 A1 | 7/2003 | Lynn et al. |
| 2003/0129239 A1 | 7/2003 | Goldshtein |
| 2003/0137067 A1 | 7/2003 | Cooper et al. |
| 2003/0157181 A1 | 8/2003 | Panzner et al. |
| 2003/0175239 A1 | 9/2003 | Margolin et al. |
| 2003/0180370 A1 | 9/2003 | Lesniak et al. |
| 2003/0211153 A1 | 11/2003 | Johnson et al. |
| 2003/0219384 A1 | 11/2003 | Donath et al. |
| 2003/0236214 A1 | 12/2003 | Wolff et al. |
| 2004/0013721 A1 | 1/2004 | Antipov et al. |
| 2004/0013738 A1 | 1/2004 | Voigt et al. |
| 2004/0014698 A1 | 1/2004 | Hortelano et al. |
| 2004/0017018 A1 | 1/2004 | Pommersheim |
| 2004/0043076 A1 | 3/2004 | Dulieu et al. |
| 2004/0047979 A1 | 3/2004 | Qiu et al. |
| 2004/0086459 A1 * | 5/2004 | Ottoboni et al. ............ 424/9.52 |
| 2004/0110898 A1 | 6/2004 | Dreja et al. |
| 2004/0195710 A1 | 10/2004 | Hubbell et al. |
| 2004/0200774 A1 | 10/2004 | Shekunov et al. |
| 2004/0202643 A1 | 10/2004 | Margolin et al. |
| 2004/0209804 A1 | 10/2004 | Govardhan et al. |
| 2004/0219224 A1 | 11/2004 | Yakovlevsky et al. |
| 2004/0241202 A1 | 12/2004 | Chluba et al. |
| 2004/0247624 A1 | 12/2004 | Unger et al. |
| 2004/0258762 A1 | 12/2004 | Boppart et al. |
| 2005/0048127 A1 | 3/2005 | Brown et al. |
| 2005/0142201 A1 | 6/2005 | Rashba-Step et al. |
| 2005/0142205 A1 | 6/2005 | Rashba-Step et al. |
| 2005/0142206 A1 | 6/2005 | Brown et al. |
| 2005/0147687 A1 | 7/2005 | Rashba-Step et al. |
| 2005/0170005 A1 | 8/2005 | Rashba-Step et al. |
| 2005/0233945 A1 | 10/2005 | Brown et al. |
| 2005/0247564 A1 | 11/2005 | Volkel et al. |
| 2005/0271732 A1 | 12/2005 | Seeney et al. |
| 2006/0018971 A1 | 1/2006 | Scott et al. |
| 2006/0024240 A1 | 2/2006 | Brown et al. |
| 2006/0024379 A1 | 2/2006 | Brown et al. |
| 2006/0260777 A1 | 11/2006 | Rashba-Step et al. |
| 2007/0092452 A1 | 4/2007 | Rashba-Step et al. |
| 2007/0207210 A1 | 9/2007 | Brown et al. |
| 2007/0258975 A1 | 11/2007 | Hagewiesche et al. |
| 2007/0281031 A1 | 12/2007 | Yang et al. |
| 2009/0017124 A1 | 1/2009 | Brown et al. |

FOREIGN PATENT DOCUMENTS

| | | |
|---|---|---|
| DE | 19812083 | 9/1999 |
| DE | 10157799 | 9/2002 |
| EP | 0223428 | 5/1987 |
| EP | 0248531 | 12/1987 |
| EP | 0377477 | 7/1990 |
| EP | 0647477 | 4/1995 |
| EP | 0809110 | 11/1997 |
| EP | 0972563 | 1/2000 |
| EP | 1060741 | 12/2000 |
| EP | 1116516 | 7/2001 |
| GB | 2334900 | 9/1999 |
| JP | 08245815 | 9/1996 |
| WO | WO-93/14110 | 7/1993 |
| WO | WO 94/18947 | 9/1994 |
| WO | WO-94/20856 | 9/1994 |
| WO | WO-95/00128 | 1/1995 |
| WO | WO-99/47252 | 9/1999 |
| WO | WO-99/47253 | 9/1999 |
| WO | WO-00/03797 | 1/2000 |
| WO | WO-00/28972 | 5/2000 |
| WO | WO-00/41679 | 7/2000 |
| WO | WO-00/77281 | 12/2000 |
| WO | WO-01/51196 | 7/2001 |
| WO | WO-01/64330 | 9/2001 |
| WO | WO-02/09864 | 2/2002 |
| WO | WO-02/09865 | 2/2002 |
| WO | WO-02/17888 | 3/2002 |
| WO | WO-02/074431 | 9/2002 |
| WO | WO-03/000014 | 1/2003 |
| WO | WO-03/015750 | 2/2003 |
| WO | WO-03/030874 | 4/2003 |
| WO | WO-03/043729 | 5/2003 |
| WO | WO-03/087384 | 10/2003 |
| WO | WO-03/090920 | 11/2003 |
| WO | WO-03/097706 | 11/2003 |
| WO | WO-2004/030649 | 4/2004 |
| WO | WO-2004/060920 | 7/2004 |
| WO | WO-2004/062784 | 7/2004 |
| WO | WO-2004/100928 | 11/2004 |
| WO | WO-2005/035088 | 4/2005 |
| WO | WO-2005/051355 | 6/2005 |
| WO | WO-2005/077414 | 8/2005 |
| WO | WO-2005/089727 | 9/2005 |
| WO | WO-2005/112885 | 12/2005 |
| WO | WO-2005/112893 | 12/2005 |
| WO | WO-2005/112894 | 12/2005 |
| WO | WO-2006/012500 A2 | 2/2006 |
| WO | WO2006/091081 * | 8/2006 |
| WO | WO-2006/091081 | 8/2006 |
| WO | WO 2006091081 A1 * | 8/2006 |

| WO | WO2007/085990 | * | 8/2007 |
| WO | WO 2007085990 A1 | * | 8/2007 |
| WO | WO-2008/068455 A1 | | 6/2008 |

OTHER PUBLICATIONS

Atlas of Chromatograms, "Separation of PEG 200 and PEG 2000," *Journal of Chromatographic Science*, 33 (1995).

Ariga et al., "Self-assembly of functional protein multilayers: from planar films to microtemplate encapsulation," pp. 367-391, IN: Malmsten (ed.), *Biopolymers at Interfaces*, 2nd ed., Marcel Dekker (2003).

Badin et al., "Clinical immunochemical study of the serum IgG fraction not precipitated in a zinc-sodium salicylate reagent," *J. Clin. Path.*, 29:984-990 (1976).

Banchereau et al., "Dendritic Cells and the Control of Immunity," *Nature*, 392:245-252 (1998).

Berton et al., "Improved Oligonucleotide Uptake and Stability by a New Drug Carrier, the SupraMolecular BioVector (SMBV)," *Biochimica et Biophysica Acta*, 1355:7-19 (1997).

Bisker-Lieb et al., "Anti-Factor VII monoclonal antibody microspheres," IN: Proceedings of the 2004 American Association of Pharmaceutical Sciences National Biotechnology Conference, p. 76 (2004).

Bisker-Lieb et al., "Uniform Microsphere Formation from Small Organic Molecules," Transactions, $31^{st}$ Annual Meeting of the Controlled Release Society, #631A (2004).

Boussif et al., "A versatile vector for gene and oligonucleotide transfer into cells in culture and in vivo: polyethylenimine," *Proc. Natl. Acad. Sci. USA*, 92:7297-7301 (1995).

Brazeau et al., "In vitro myotoxicity of selected cationic macromolecules used in non-viral gene delivery," *Pharm. Res.*, 15:680-684 (1998).

Brown et al., "PROMAXX microsphere characterization," IN: *Proceedings of the Ninth Biennial Respiratory Drug Delivery Conference*, pp. 477-479 (2004).

Brown et al., "Pulmonary delivery of novel insulin microspheres," IN: *Proceedings of the Eighth Biennial Respiratory Drug Delivery Conference*, pp. 431-434 (2002).

Bustami et al., "Generation of micro-particles of proteins for aerosol delivery using high pressure modified carbon dioxide," *Pharm. Res.*, 17:1360-1366 (2000).

Byrne et al., "Dendritic cells: making progress with tumour regression?" *Immunol. Cell Biol.*, 80:520-530 (2002).

Chamarthy et al., "A cationic peptide consists of ornithine and histidine repeats augments gene transfer in dendritic cells," *Mol. Immunol.*, 40:483-490 (2003).

Check, "A tragic setback," *Nature*, 420:116-118 (2002).

Chollet et al., "Side-effects of a systemic injection of linear polythylenimine-DNA complexes," *J. Gene Med.*, 41:84-91 (2002).

Chu et al., "Efficiency of cytoplasmic delivery by pH-sensitive liposomes to cells in culture," *Pharm. Res.*, 7:824-834 (1990).

Coombes et al., "Lactic Acid-Stabilised Albumin for Microsphere Formulation and Biomedical Coatings," *Biomaterials*, 22:1-8 (2001).

Couvreur et al., "pH-sensitive liposomes: an intelligent design system for the delivery of antisense oligonucleotides," *J. Liposome Res.*, 7:1-18 (1997).

Crystal, "Transfer of genes to humans: early lessons and obstacles for success," *Science*, 270:404-410 (1995).

Daneshvar, "High-Pressure Phase Equilibria of Poly(ethylene glycol)-Carbon Dioxide Systems," *J. Phys. Chem.*, 94:2124-2128 (1990).

Dokka et al., "Inhibition of endotoxin-induced lung inflammation by interleukin-10 gene transfer in mice," *Am. J. Physiol. Lung Cell Mol. Physiol.*, 279:L872-L877 (2000).

Eliassi et al., "Densities of poly(ethylene glycol) + water mixtures in the 298.15-328.15 K temperature," *J. Chem. Eng. Data*, 43:719-721 (1998).

Felgner et al., "Cationic liposome-mediated transfection," *Nature*, 337:387-388 (1989).

Glorioso et al., "Development of herpes simplex virus vectors for gene transfer to the central nervous system," pp. 281-302, IN: WOLFF (ed.), *Gene Therapeutics: Methods and Applications of Direct Gene Transfer* (1993).

Govardhan et al., "Novel long-acting crystal formulation of human growth hormone," *Pharm. Res.*, 22:1461-1470 (2005).

Hagen et al., "Separation of Oligomers of Polyethylene Glycols by Supercritical Fluid Chromatography," *J. Microcol. Sep.*, 3:27-31 (1991).

Harrison et al., "Effect of Surfactants on the Interfacial Tension Between Supercritical Carbon Dioxide and Polyethylene Glycol," *Langmuir*, 12:2637-2644 (1996).

Hudson et al., "Biodegradable polymer matrices for the sustained exogenous delivery of a biologically active c-myc hammerhead ribozymes," *Int. J. Pharm.*, 136:23-29 (1996).

Hughes et al., "Evaluation of adjuvants that enhance the effectiveness of antisense oligodeoxynucleotides," *Pharm. Res.*, 13:404-410 (1996).

Hwang et al., "Cationic polymers for gene delivery: designs for overcoming barriers to systemic administration," *Curr. Opin. Mol. Ther.*, 3:183-191 (2001).

Jakoby, *Enzyme Purification and Related Techniques. Methods in Enzymology*. vol. XXII. New York: Academic Press (1971). Table of Contents Only.

Johnston et al., "Supercritical Fluid Science and Techology," *ACS Symposium Series 406*, pp. 72-85 (1988).

Kabanov et al., "Water-soluble block polycations as carriers for oligonucleotide delivery," *Bioconjugate Chem.*, 6:639-647 1995.

Kataoka et al., "Spontaneous formation of polyion complex micelles with narrow distribution from antisense oligonucleotide and cationic block copolymer in physiological saline," *Macromolecules*, 29:8556-8557 (1996).

King, "Supercritical Fluid Extraction of Polymers and Solvents: Utilization of the Solubility Parameter Concept," CPC International, Moffett Technical Center, pp. 707-712.

Kinugasa et al., "Separation of Poly(ethylene glycol)s by Supercritical Fluid Chromatography," Abstract Only.

Kroschwitz (ed.), *Kirk-Othmer Encyclopedia of Chemical Technology*, vol. 23, pp. 452-477, New York: John Wiley and Sons (1997).

Larionova et al., "Encapsulation of proteins in polyelectrolyte microcapsules. Factors regulating the protein release," *Proc. Intl. Symp. Control. Rel. Bioact. Mater.*, 28:1398-1399 (2001).

Leach et al., "Encapsulation of protein nanoparticles into uniform-sized microspheres formed in a spinning oil film," *AAPS PharmSciTech*, 6:E605-E617 (2005).

Leaversuch, "Materials renewable PLA polymer gets 'green light' for packaging uses." pp. 1-4. Retrieved from the Internet in Mar. 2002, <URL:http://www.ptonline.com/articles/200203fa2.html>.

Legendre. "Delivery of plasmid DNA into mammalian cell lines using pH-sensitive liposomes: comparison with cationic liposomes," *Pharm. Res.*, 9:1235-1242 (1992).

Loke et al., "Delivery of c-myc antisense phosphorothioate oligodeoxynucleotides to hematopoietic cells in culture by liposome fusion: specific reduction in c-myc protein expression correlates with inhibition of cell growth and DNA synthesis," *Curr. Top. Microbiol. Immunol.*, 141:282-289 (1988).

Lvov et al., "Nanoengineered shells for encapsulation and controlled release," pp. 1-3, NSF Nanoscale Science and Engineering Grantees Conference (Dec. 16-18, 2003).

Mahato et al., "Cationic lipid-based gene delivery systems: pharmaceutical perspectives," *Pharm. Res.*, 14:853-859 (1997).

Meiri et al., "Reversible antisense inhibition of Shaker-like Kv1.1 potassium channel expression impairs associative memory in mouse and rat," *Proc. Natl. Acad. Sci. USA*, 94:4430-4434 (1997).

Middaugh, "Oligonucleotide delivery," IN: Mathiowitz (ed.), *Encyclopedia of Controlled Drug Delivery*, vol. 2, pp. 691-697, John Wiley & Sons (1999).

Miller, "Human gene therapy comes of age," *Nature*, 357:455-460 (1992).

Moghimi, "Chemical camouflage of nanospheres with a poorly reactive surface: towards development of stealth and target-specific nanocarriers," *Biochimica et Biophysica Acta*, 1590:131-139 (2000).

Morita et al., "Formation and isolation of spherical fine protein microparticles through lyophilization of protein-poly (ethylene glycol) aqueous mixture," *Pharm. Res.*, 17:1367-1373 (2000).

Oberhouser et al., "Enhancing endosomal exit of nucleic acids using pH-sensitive viral fusion peptides," pp. 247-266, IN: Akhtar (ed.), *Delivery Strategies for Antisense Oligonucleotides Therapeutics*, Boca Raton, FL: CRC Press (1995).

Pargaonkar et al., "Controlled release of dexamethasone from microcapsules produced by polyelectrolyte layer by layer nanoassembly," *Pharm. Res.*, 22:826-835 (2005).

Perlaky et al., "Growth inhibition of human tumor cell lines by antisense oligonucleotides designed to inhibit p120 expression," *Anti-Cancer Drug Des.*, 8:3-14 (1993).

Pommersheim et al., "Immobilization of enzymes by multilayer microcapsules," *Macromol. Chem. Phys.*, 195:1557-1567 (1994).

Qiu et al., "Studies on the drug release properties of polysaccharide multilayers encapsulated ibuprofen microparticles," *Langmuir*, 17:5375-5380 (2001).

Radler et al., "Structure of DNA-cationic liposome complexes: DNA intercalation in multilamellar membranes in distinct interhelical packing regimes," *Science*, 275:810-814 (1997).

Rashba-Step et al., "Albumin microspheres as drug delivery vehicle for multiple routes of administration," *Proceedings of the Intl. Symp. Control. Rel. Bioact. Mat.*, vol. 28 (2001).

Rashba-Step et al., "PROMAXX protein matrix microspheres for delivery of alpha-1 antitrypsin via the pulmonary route," *Transactions 31st Annual Meeting Control. Rel. Soc.*, #474 (2004).

Sah et al., "Biodegradable microcapsules prepared by a w/o/w technique: effects of shear force to make a primary w/o emulsion on their morphology and protein release," *J. Microencap.*, 12:59-69 (1995).

Schwartz et al., "Synthetic DNA-compacting peptides derived from human sequence enhance cationic lipid-mediated gene transfer in vitro and in vivo," *Gene Ther.*, 6:282-292 (1999).

Sinha et al., "Biodegradable microspheres for protein delivery," *J. Control. Rel.*, 90:261-280 (2003).

Sukhorukov et al., "Controlling release and permeability properties of militilayer [sic] polyelectrolyte capsules," *Proc. Intl. Symp. Control. Rel. Bioact. Mater.*, 28:1402-1403 (2001).

Sunkara et al., "Supercritical Fluids: Drug Delivery Applications of Supercritical Fluid Technology," Drug Delivery Technology, Retrieved from the Internet on Jul. 13, 2006: URL:http://www.drugdelievervtech.com/cgi.bin/articles.cgi?idArticle=14.

Sweeney et al., "Efficient therapeutic gene delivery after systemic administration of a novel polyethylenimine/DNA vector in an orthotopic bladder cancer model," *Cancer Res.*, 63:4017-4020 (2003).

Thierry et al., "Overcoming multidrug resistance in human tumor cells using free and liposomally encapsulated antisense oligodeoxynucleotides," *Biochem. Biophys. Res. Commun.*, 190:952-960 (1993).

Tiourina et al., "Encapsulation of alpha chymotrypsin onto the hollow polyelectrolyte microcapsules," *Proc. Intl. Symp. Control. Rel. Bioact. Mater.*, 28:1400-1401 (2001).

Tiyaboonchai et al., "Formulation and characterization of DNA-polyethylenimine-dextran sulfate nanoparticles," *Eur. J. Pharm. Sci.*, 19:191-202 (2003).

Tomlinson et al., "Controllable gene therapy: pharmaceutics of non-viral gene delivery systems," *J. Control. Rel.*, 39:357-372 (1996).

Vanderkerken et al., "Synthesis and evaluation of poly(ethylene glycol)-polylysine block copolymers as carriers for gene delivery," *J. Bioactive Compatible Polymers*, 15:115-138 (2000).

Vanderlubben et al., "Chitosan microparticles for mucosal vaccination against diphtheria: oral and nasal efficacy studies in mice," *Vaccine*, 21:1400-1408 (2003).

Van Drooge et al., "Incorporation of lipophilic drugs in sugar glasses by lyophilization using mixture of water and tertiary butyl alcohol as solvent," *J. Pharm. Sci.*, 93:713-725 (2004).

Wittaya-Areekul et al., "Freeze-drying of tert-butanol/water cosolvent systems: a case report on formation of a friable freeze-dried powder of tobramycin sulfate," *J. Pharm. Sci.*, 91:1147-1155 (2002).

Yamakawa et al., "Release Behavior of Poly(Lactic Acid-co-Glycolic Acid) Implants Containing Phosphorothioate Oligodeoxnucleotide," *Biol. Pharm. Bull.*, 20:455-459 (1997).

Yang et al., "Crystalline monoclonal antibodies for subcutaneous delivery," *Proc. Natl. Acad. Sci. USA*, 100:6934-6939 (2003).

Yang et al., "Layer by layer construction of novel biofunctional fluorescent microparticles for immunoassay applications," *J. Colloid Interface Sci.*, 234:356-362 (2001).

Yang et al., "Novel fluorescent labels prepared by layer to layer assembly on colloids for biodetection systems," *Mat. Res. Soc. Symp. Proceed.*, 667:G5.5.1-G5.5.6 (2001).

Zahr et al., "Fabrication of core-shell drug nanoparticles for therapeutic delivery," *Polymeric Materials: Science and Engineering*, 93:802-803 (2005).

Zelphati et al., "Mechanism of oligonucleotide release from cationic lipids," *Proc. Natl. Acad. Sci. USA*, 100:11493-11498 (1996).

Zhao et al., "Modulation of oligonucleotide-induced immune stimulation by cyclodextrin analogs," *Biochem. Pharmacol.*, 52:1537-1544 (1996).

International Search Report and Written Opinion from corresponding International Application No. PCT/US2009/054525, dated Mar. 8, 2010.

International Preliminary Report on Patentability for corresponding International Application No. PCT/US09/54525, dated Jan. 21, 2011.

Nonfinal office Action from U.S. Appl. No. 12/195,092, dated Mar. 11, 2011.

Badin et al., "Methode de dosage des gamma-globulines par precipitation zincique en milieu de force ionique elevee: Comparaison avec l'electrophorese, la precipitation en solution zincique diluee et le relargage au sulfate d'ammonium," Path. et Biol., 11:195-201 (1963).

Badin et al., "Precipitation des gamma globulines dans un reactif associant le zinc et le salicylate de soude. Nature des precipites. Effets des inhibiteurs de la floculation en fonction de la force ionique. " Bull. Soc. Chem. Biol., 43:387-408 (1961).

Badin, "Individualite d'une fraction de gammaG-Globulines non precipitables par le zinc a pH 7.3," Clin. Chim. Acta, 19 :11-18 (1968). [French].

US 5,849,884, 12/1998, Woiszwillo et al. (withdrawn)

\* cited by examiner

METHODS OF PROCESSING MULTI-PHASIC DISPERSIONS

TECHNICAL FIELD

The present disclosure relates to multi-phasic dispersions, and more particularly, to methods of processing such dispersions.

DESCRIPTION OF RELATED TECHNOLOGY

Microparticles, microspheres, and microcapsules, referred to herein collectively as "microparticles," are solid or semi-solid particles having a diameter of less than one millimeter, more preferably less than 100 microns, which can be formed of a variety of materials, including but not limited to various polymers and proteins. Microparticles have been used in many different applications, primarily separations, diagnostics, and drug delivery.

The most well known examples of microparticles used in separations techniques are those which are formed of polymers of either synthetic or protein origin, such as polyacrylamide, hydroxyapatite, or agarose. These polymeric microparticles are commonly used to separate molecules such as proteins based on molecular weight and/or ionic charge, or by interaction with molecules chemically coupled to the microparticles.

In the diagnostic area, spherical beads or particles have been commercially available as a tool for biochemists for many years. For example, microparticles have been derivatized with an enzyme, a substrate for an enzyme, or a labeled antibody, and then interacted with a molecule to be detected, either directly or indirectly. A number of derivatized beads are commercially available with various constituents and sizes.

In the controlled drug delivery area, molecules have been encapsulated within microparticles or incorporated into a matrix to provide controlled release of the molecules. A number of different techniques have been used to make such microparticles from various polymers including phase separation, solvent evaporation, emulsification, and spray drying. Generally, the polymers form the supporting structure of the microparticles, and the drug or molecule of interest is incorporated into the supporting structure. Exemplary polymers used for the formation of microparticles include homopolymers and copolymers of lactic acid and glycolic acid (PLGA), block copolymers, and polyphosphazenes.

U.S. Patent Publication No. 2005/0142205 (the '205 publication) discloses phase separation methods for forming microparticles involving dissolving an active agent in an aqueous and/or aqueous-miscible solvent(s) containing a dissolved phase-separation enhancing agent(s) to form a solution in a single liquid phase. The solution is then subjected to a liquid-solid phase separation to cause the active agent to form solid spherical small particles (i.e., the solid phase) while the phase-separation enhancing agent(s) and solvent(s) comprise the liquid phase. The '205 publication discloses methods of harvesting microparticles including washing solutions and/or dry powders comprising microparticles with liquid media in which the active agent is insoluble and the (undesired) phase-separation enhancing agent is soluble. Disclosed liquid media include organic solvents and supercritical fluids. Representative washing methods include diafiltration and centrifugation. The remaining liquid phases are then typically removed by lyophilization or evaporation.

SUMMARY OF THE INVENTION

In one embodiment, the methods of processing multi-phasic dispersions comprise providing a multi-phasic dispersion including dispersed and continuous phases, the dispersion comprising solid microparticles and at least a first non-volatile material, providing a non-solvent, combining the multi-phasic dispersion and the non-solvent, and selectively effecting migration of the microparticles into or through the non-solvent such that a majority of the microparticles is separated from the dispersion, wherein the microparticles are substantially insoluble in the non-solvent and the non-solvent has either a density which is greater than that of the continuous phase or a viscosity which is greater than that of the continuous phase.

In another embodiment, the methods of processing multi-phasic dispersions comprises providing a multi-phasic dispersion including dispersed and continuous phases, the dispersion comprising solid microparticles and a first non-volatile material at a first concentration, providing a non-solvent comprising a second non-volatile material at a second concentration that is greater than the first concentration, wherein the microparticles are substantially insoluble in the non-solvent, combining the multi-phasic dispersion and the non-solvent, and selectively effecting migration of the microparticles into or through the non-solvent such that a majority of the microparticles is separated from the dispersion.

DETAILED DESCRIPTION OF THE INVENTION

The present disclosure relates to multi-phasic dispersions, and more particularly, to methods for processing such dispersions. Specifically, the disclosure relates to processes of separating a dispersed phase comprising microparticles from reaction/incubation media so that the microparticles can be collected and/or incorporated into compositions and formulations suitable for drug delivery, diagnostics, separations, and other applications.

The disclosed methods are advantageous for a number of reasons including but not limited to (1) a reduction in microparticle aggregation can be achieved (relative to known methods for processing microparticles); (2) the microparticles can be formulated with/into a pharmaceutically acceptable diluent to provide a composition capable of being administered to a subject without performing a costly and time-consuming drying step such as lyophilization or evaporation; and (3) purification and isolation of the microparticles can be achieved relatively easily (relative to known methods of processing microparticles).

In one embodiment, the methods of processing multi-phasic dispersions comprise providing a multi-phasic dispersion including dispersed and continuous phases, the dispersion comprising solid microparticles and at least a first non-volatile material, providing a non-solvent, combining the multi-phasic dispersion and the non-solvent, and selectively effecting migration of the microparticles into or through the non-solvent such that a majority of the microparticles is separated from the dispersion, wherein the microparticles are substantially insoluble in the non-solvent and the non-solvent has either a density which is greater than that of the continuous phase or a viscosity which is greater than that of the continuous phase.

In another embodiment, the methods of processing multi-phasic dispersions comprises providing a multi-phasic dispersion including dispersed and continuous phases, the dispersion comprising solid microparticles and a first non-volatile material at a first concentration, providing a non-solvent comprising a second non-volatile material at a second concentration that is greater than the first concentration, wherein the microparticles are substantially insoluble in the non-solvent, combining the multi-phasic dispersion and the non-solvent, and selectively effecting migration of the microparticles into or through the non-solvent such that a majority of the microparticles is separated from the dispersion.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a microparticle is a reference to one such microparticle or a plurality of such microparticles, including equivalents thereof known to one skilled in the art. Also, as used herein and in the claims, the terms "at least one" and "one or more" have the same meaning and include one, two, three or more. The following terms, unless otherwise indicated, shall be understood to have the following meanings when used in the context of the present disclosure.

"Dispersion" refers to a mixture of matters having at least one dispersed or discontinuous phase (optionally, being finely divided, such as in the form of solid microparticles) present in a solid or non-solid continuous phase (e.g., fluidic, liquid, aqueous, organic, gaseous). Representative examples of dispersions in accordance with the disclosure include solid in solid, solid in liquid, solid in gas, and the like. A dispersion can be substantially homogenous or non-homogenous. A suspension is a particular dispersion in which the discontinuous solid phase (such as microparticles) can remain stably suspended (substantially free of sedimentation) in the continuous phase for extended periods of time (for example, at least 5 seconds, 10 seconds, or 30 seconds, e.g., minutes, hours, days, weeks, months, or even one year or more). "Multiphasic dispersions" are dispersions having at least two phases, for example, three or even more phases. In one example, such dispersions may comprise two immiscible solvents or solvent systems in addition to a dispersed phase.

"Microparticle" refers to a solid particulate (including substantially solid or semi-solid, but excluding gel, liquid and gas) having an average geometric particle size (sometimes referred to as diameter) of less than about 1 mm, for example, less than about 200 microns, less than about 100 microns, less than about 10 microns, less than about 1 micron, less than about 100 nm, less than about 10 nm, greater than about 0.1 nm, greater than about 1 nm, and ranges between these values. Thus, suitable ranges for average geometric particle size include about 0.1 nm to about 1 mm, about 1 nm to about 1 mm, about 10 nm to about 1 mm, about 100 nm to about 1 mm, about 1 micron to about 1 mm, about 10 microns to about 1 mm, about 100 microns to about 1 mm, about 200 microns to about 1 mm, about 0.1 nm to about 200 microns, about 1 nm to about 200 microns, about 10 nm to about 200 microns, about 100 nm to about 200 microns, about 1 micron to about 200 microns, about 10 microns to about 200 microns, about 100 microns to about 200 microns, about 0.1 nm to about 100 microns, about 1 nm to about 100 microns, about 10 nm to about 100 microns, about 100 nm to about 100 microns, about 1 micron to about 100 microns, about 10 microns to about 100 microns, about 0.1 nm to about 10 microns, about 1 nm to about 10 microns, about 10 nm to about 10 microns, about 100 nm to about 10 microns, about 1 micron to about 10 microns, about 0.1 nm to about 1 micron, about 1 nm to about 1 micron, about 10 nm to about 1 micron, about 100 rim to about 1 micron, about 0.1 nm to about 100 nm, about 1 nm to about 100 nm, about 10 nm to about 100 nm, about 0.1 nm to about 10 nm, about 1 nm to about 10 nm, and/or about 0.1 nm to about 1 nm. Average geometric particle size can be measured by dynamic light scattering methods (such as photocorrelation spectroscopy, laser diffraction, low-angle laser light scattering (LALLS), medium-angle laser light scattering (MALLS)), light obscuration methods (such as Coulter analysis method), or other methods (such as rheology, light or electron microscopy). Microparticles for pulmonary delivery have an aerodynamic particle size as determined by time of flight measurements or Andersen Cascade Impactor measurements. Microparticles having a spherical shape are sometimes referred to as microspheres and nanospheres. Microparticles having an encapsulated structure are sometimes referred to as microcapsules and nanocapsules. Microparticles can be porous, for example, having one or more internal voids and/or cavities. Other microparticles are non-porous and/or are free of such voids or cavities. Microparticles are formed from, in part or in whole, one or more materials including but not limited to active agents, carriers, polymers, complexing agents, stabilizing agents, excipients, ions, moisture, residual solvents, impurities, by-products, and/or manufacturing-related compounds. Microparticles can be crystalline, amorphous, microcrystalline, nanocrystalline, or a combination thereof.

"Active agent" refers to naturally occurring, recombinant, synthetic, or semi-synthetic materials (e.g., compounds, fermentates, extracts, cellular structures) capable of eliciting, directly or indirectly, one or more physical, chemical, and/or biological effects, in vitro and/or in vivo. The active agent can be capable of preventing, alleviating, treating, and/or curing abnormal and/or pathological conditions of a living body, such as by destroying a parasitic organism, or by limiting the effect of a disease or abnormality by materially altering the physiology of the host or parasite. The active agent can be capable of maintaining, increasing, decreasing, limiting, or destroying a physiological body function. The active agent can be capable of diagnosing a physiological condition or state by an in vitro and/or in vivo test. The active agent can be capable of controlling or protecting an environment or living body by attracting, disabling, inhibiting, killing, modifying, repelling and/or retarding an animal or microorganism. The active agent can be capable of otherwise treating (such as deodorizing, protecting, adorning, grooming) a body. Depending on the effect and/or its application, the active agent can further be referred to as a bioactive agent, a pharmaceutical agent (such as a prophylactic agent, a therapeutic agent), a diagnostic agent, a nutritional supplement, and/or a cosmetic agent, and includes, without limitation, examples such as prodrugs, affinity molecules, synthetic organic molecules, polymers, molecules with a molecular weight of 2 kDa or less (such as those having a molecular weight of less than about 1.5 kDa, or less than about 1kDa), macromolecules (such as those having a molecular weight of greater than about 2 kDa, for example, greater than about 5 kDa or between about 2 kDa and 5 kDa), proteinaceous compounds, peptides, vitamins, steroids, steroid analogs, lipids, nucleic acids, carbohydrates, precursors thereof, and derivatives thereof. Active agents can be ionic or non-ionic, can be neutral, positively charged, negatively charged, or zwitterionic, and can be used singly or in combination of two or more thereof. Active agents can be water-insoluble or water-soluble. Active agents can have an isoelectric point of 7.0 or greater, or less than 7.0.

"Proteinaceous compounds" refer to natural, synthetic, semi-synthetic, or recombinant compounds of or related structurally and/or functionally to proteins, such as those containing or consisting essentially of α-amino acids covalently associated through peptide linkages. Non-limiting proteinaceous compounds include globular proteins (e.g., albumins, globulins, histones), fibrous proteins (e.g., collagens, elastins, keratins), compound proteins (including those containing one or more non-peptide components, e.g., glycoproteins, nucleoproteins, mucoproteins, lipoproteins, metalloproteins), therapeutic proteins, fusion proteins, receptors, antigens (such as synthetic or recombinant antigens), viral surface proteins, hormones and hormone analogs, antibodies (such as monoclonal or polyclonal antibodies), enzymes, Fab fragments, cyclic peptides, linear peptides, and the like. Non-limiting therapeutic proteins include bone morphogenic proteins, drug resistance proteins, toxoids, erythropoietins, proteins of the blood clotting cascade (e.g., Factor VII, Factor VIII, Factor IX, et al.), subtilisin, ovalbumin, alpha-1-antitrypsin (AAT), DNase, superoxide dismutase (SOD), lysozymes, ribonucleases, hyaluronidase, collagenase, human growth hormone (hGH), erythropoietin, insulin, insulin-like growth factors, interferons, glatiramer, granulocyte-macrophage colony-stimulating factor, granulocyte colony-stimulating factor, desmopressin, leutinizing hormone release hormone (LHRH) agonists (e.g., leuprolide, goserelin, buserelin, gonadorelin, histrelin, nafarelin, deslorelin, fertirelin, triptorelin), LHRH antagonists, vasopressin, cyclosporine, calcitonin, parathyroid hormone, parathyroid hormone peptides, glucogen-like peptides, and analogs thereof. Proteinaceous compounds may be neutral, positively charged, negatively charged, or zwitterionic, and may be used singly or in combination of two or more thereof.

"Nucleic acids" refer to natural, synthetic, semi-synthetic, or recombinant compounds formed at least in part from two or more of the same or different nucleotides, and may be single-stranded or double-stranded. Non-limiting examples of nucleic acids include oligonucleotides (such as those having 20 or less base pairs, e.g., sense, anti-sense, or missense), aptamers, polynucleotides (e.g., sense, anti-sense, or missense), DNA (e.g., sense, anti-sense, or missense), RNA (e.g., sense, anti-sense, or missense), siRNA, nucleotide acid constructs, single-stranded or double-stranded segments thereof, as well as precursors and derivatives thereof (e.g., glycosylated, hyperglycosylated, PEGylated, FITC-labeled, nucleosides, salts thereof). Nucleic acids may be neutral, positively charged, negatively charged, or zwitterionic, and may be used singly or in combination of two or more thereof.

"Macromolecule" refers to a material capable of providing a three-dimensional (e.g., tertiary and/or quaternary) structure, and includes carriers and certain active agents of the present disclosure. Macromolecules typically have a molecular weight of 2 kD or greater, for example, greater than 5 kD or between 2 kD and 5 kD. Non-limiting macromolecules used to form the microparticles include, inter alia, polymers, copolymers, proteins (e.g., enzymes, recombinant proteins, albumins such as human serum albumin, monoclonal antibodies, polyclonal antibodies, proteinaceous compounds), peptides, lipids, carbohydrates (e.g., monosaccharides, disaccharides, polysaccharides), nucleic acids, vectors (e.g., viruses, viral particles), and complexes and conjugates thereof (e.g., covalent and/or non-covalent associations between two macromolecules such as carbohydrate-protein complexes or conjugates, or between an active agent and a macromolecule such as hapten-protein complexes or conjugates). Macromolecules may be neutral, positively charged, negatively charged, or zwitterionic, and may be used singly or in combination of two or more thereof.

"Carrier" refers to a compound, typically a macromolecule, having a primary function to provide a three-dimensional structure (including tertiary and/or quaternary structure) to the microspheres. The carrier may be unassociated or associated with the active agent (such as conjugates or complexes thereof) in forming microparticles as described above. The carrier may further provide other functions, such as being an active agent, modifying a release profile of the active agent from the microparticle, and/or imparting one or more particular properties to the microparticle (such as contribute at least in part to the net surface charge). In one example, the carrier is a protein (e.g., an albumin such as human serum albumin) having a molecular weight of 1500 Daltons or greater.

"Polymer" or "polymeric" refers to a natural, recombinant, synthetic, or semi-synthetic molecule having in at least one main chain, branch, or ring structure two or more repeating monomer units. Polymers broadly include dimers, trimers, tetramers, oligomers, higher molecular weight polymers, adducts, homopolymers, random copolymers, pseudo-copolymers, statistical copolymers, alternating copolymers, periodic copolymers, bipolymers, terpolymers, quaterpolymers, other forms of copolymers, substituted derivatives thereof, and mixtures thereof. In one aspect, the terms polymer and polymeric refer to molecules having 10 or more repeating monomer units. Polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric, can be ionic or non-ionic, can be neutral, positively charged, negatively charged, or zwitterionic, and can be used singly or in combination of two or more thereof.

"Spherical" refers to a geometric shape that is at least "substantially spherical." "Substantially spherical" means that the ratio of the longest length (i.e., one between two points on the perimeter and passes the geometric center of the shape) to the shortest length on any cross-section that passes through the geometric center is less than about 1.5, such as less than about 1.33, or less than about 1.25. Thus, spherical does not require a line of symmetry. Further, the microparticles can have surface texturing (such as continuous or discrete lines, islands, lattice, indentations, channel openings, protuberances that are small in scale when compared to the overall size of the microparticles) and still be considered spherical. Surface contact between microparticles is minimized when the microparticles are spherical, and thus undesirable agglomeration of the microparticles is typically minimized. In comparison, microparticles that are aspherical crystals or flakes typically display observable agglomeration through ionic and/or non-ionic interactions at relatively large flat surfaces.

"Solid" refers to a state that includes at least substantially solid and/or semi-solid, but excludes liquid and gas.

"Ambient temperature" refers to a temperature of around room temperature, typically in a range of about 20° C. to about 40° C., for example, about 20° C. to about 25° C.

"Formed from" and "formed of" denote open language. As such, it is intended that a composition formed from or formed of a list of recited components be a composition comprising at least these recited components, and can further include other non-recited components during formulation of the composition and/or in the final obtained product.

Unless otherwise expressly specified, all of the numerical ranges, amounts, values and percentages such as those for quantities of materials, times, temperatures, reaction conditions, ratios of amounts, values for molecular weight (whether number average molecular weight $M_n$ or weight average molecular weight $M_w$), and others disclosed herein should be understood as modified in all instances by the term "about," if about is not expressly used in combination with said ranges, amounts, values, and percentages herein. Accordingly, unless indicated to the contrary, the numerical parameters set forth in the present disclosure and attached claims are approximations that can vary. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, is inherently somewhat uncertain because of the standard deviation found in its respective testing measurement. Furthermore, when numerical ranges of varying scope are set forth herein, it is contemplated that any combination of these values inclusive of the recited values can be used in accordance with the teachings of the disclosure.

Examples provided herein, including those following "such as" and "e.g.," are considered as illustrative only of various aspects and features of the present disclosure and embodiments thereof, and thus should not alter the scope of any of the referenced terms or phrases. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner as understood by one of ordinary skill in the art.

Microparticles

Non-limiting microparticles, materials and methods for fabricating microparticles, compositions and formulations containing microparticles, and utilities of such microparticles, compositions, and formulations include those disclosed in U.S. Pat. Nos. 5,525,519, 5,554,730, 5,578,709, 5,599,719, 5,981,719, 6,090,925, 6,268,053, and 6,458, 387, U.S. Publication Nos. 20030059474, 20030064033, 20040043077, 20050048127, 20050142201, 20050142205, 20050142206, 20050147687, 20050170005, 20050233945, 20060018971, 20060024240, 20060024379, 20060260777, 20070092452, 20070207210, and 20070281031, the disclosures of which are herein incorporated by reference in their entirety. Microparticles can have a generally uniform size distribution, such as a monodisperse size distribution, or a polydisperse size distribution, and a generally uniform shape, such as being substantially spherical. One or more characteristics of the microparticles can be adjusted during fabrication by manipulating one or more variables such as, but not limited to, selection of ingredients or combination thereof, concentrations of different ingredients, reaction temperature, reaction time, and/or pH if reaction is taken place in aqueous solution.

Microparticles are suitable for delivering, in vivo, ex vivo, and/or in vitro, one active agent or a combination of two or more active agents with rapid and/or controlled release profiles, and are useful for a wide variety of therapeutic, pharmaceutical, diagnostic, medical, medicinal, cosmetic, nutritional, biocidic, separational, industrial, commercial, and research applications, such as drug delivery, vaccination, gene therapy and histopathological or in vivo tissue or tumor imaging. Microparticles can be formulated for oral, parenteral, mucosal; ophthalmic; intravenous, subcutaneous, subdermal, intradermal, intra-articular, intramuscular, pulmonary (including oral and nasal inhalations), and/or topical administrations to a subject. Intravenous administration includes catheterization and angioplasty.

The microparticles typically contain one or more macromolecules. The one or more macromolecules (typically, one or more bioactive macromolecules and/or one or more carrier macromolecules) may comprise at least 1%, 5%, 10%, 20%, 30%, 40%, 50%, 60%, 70%, 80%, 90%, 95%, or 98%, and up to 100%, or less than 100%, by weight and/or volume of the microparticle, or be present in a range between any two of such values. It will be understood by those skilled in the art that the macromolecule can be a portion (e.g., fragment, segment, subunit) of another larger macromolecule. It will be further understood that macromolecules include affinity molecules, which can be, for example, the receptor or ligand portions of a receptor-ligand interaction. Non-limiting examples of ligands include viruses, bacteria, polysaccharides, or toxins that act as antigens to generate immune responses when administered to an animal and cause the production of antibodies.

One or more ingredients other than the macromolecules described above and the active agents described below including but not limited to polymers, complexing agents, stabilizing agents, excipients, ions, moisture, residual solvents, impurities, by-products, may be present in the microparticle at a quantity of 50% or less, 30% or less, 20% or less, 10% or less, 5% or less, or 2% or less, or greater than 0%, by weight and/or volume of the microparticle, or in a range between any two of such values. Additionally, any ingredients present in the reaction/incubation medium (e.g., such as non-volatile materials) during the formation of the microparticles can be substantially removed from and thus absent in the resulting microparticles. Immediately or at a later stage following their formation (which may or may not be in-situ), the microparticles may be dispersed (e.g., as colloids or suspensions) in a continuous solid phase (e.g., a frozen solid comprising the dispersion) or in a non-solid phase (e.g., a flowable medium, such as the reaction/incubation medium in which the microparticles are formed, or a washing medium).

The microparticles may have a density substantially the same as or different from (such as greater than or less than) that of the continuous phase (measured at the same temperature, such as ambient temperature). Densities of the microparticles, and the continuous phase equal their respective weight divided by their respective volume. The microparticles may have a density less than, equal to, or greater than values such as 0.8 g/cm$^3$, 0.95 g/cm$^3$, 1.0 g/cm$^3$, 1.05 g/cm$^3$, 1.1 g/cm$^3$, 1.3 g/cm$^3$, 1.35 g/cm$^3$, 1.5 g/cm$^3$, and 1.9 g/cm$^3$, or in a range between any two of such values, such as between 1.0 g/cm$^3$ and 1.5 g/cm$^3$ or between 1.2 g/cm$^3$ and 1.5 g/cm$^3$. Density of the microparticles may be measured by helium pycnometry at ambient temperature, by density-gradient techniques (e.g., using centrifugation or ultracentrifugation) using suitable gradient medium (e.g., salts of alkali metals such as NaCl, NaBr, NaI, KBr, CsF, CsCl, CsBr, cesium sulfate, cesium acetate, cesium trifluoroacetate, RbCl, and potassium tartrate; neutral, water-soluble molecules such as sucrose with optional addition of glucose, glycerol, or mineral oil; hydrophilic macromolecules such as dextran, sucrose-epichlorohydrin copolymer, and bovine serum albumin; other synthetic molecules such as sodium or methyl glucamine salts of triiodobenzoic acid and of metrizoic acid, and metrizamide), and other known methods. Standard methods involving density-gradient techniques include ASTM D1505-03, ASTM D1505-98, and ISO 1183-2.

Active Agents

One or more active agents are typically covalently and/or non-covalently associated with, and/or entrapped by, at least a portion (e.g., the center or core, one or more specifically or randomly distributed compartments, inner and/or outer surfaces) of the microparticle. For example, the one or more active agents may be covalently and/or non-covalently associated with, and/or entrapped by, at least a portion or substantially all of one or more macromolecules (e.g., bioactive macromolecules and/or carrier macromolecules) and/or one or more other ingredients (e.g., with one or more polymers, as complexes or conjugates thereof).

The active agent may be a pharmaceutical agent. Depending on its effect and/or application, the pharmaceutical agent includes, without limitation, adjuvants, adrenergic agents, adrenergic blocking agents, adrenocorticoids, adrenolytics, adrenomimetics, alkaloids, alkylating agents, allosteric inhibitors, anabolic steroids, analeptics, analgesics, anesthetics, anorexiants, antacids, anti-allergic agents, antiangiogenesis agents, anti-arrhythmic agents, anti-bacterial agents, antibiotics, antibodies, anticancer agents such as paclitaxel and derivative compounds, anticholinergic agents, anticholinesterases, anticoagulants, anticonvulsants, antidementia agents, antidepressants, antidiabetic agents, antidiarrheals, antidotes, antiepileptics, antifolics, antifungals, antigens, antihelmintics, antihistamines, antihyperlipidemics, antihypertensive agents, anti-infective agents, anti-inflammatory agents, antimalarials, antimetabolites, antimuscarinic agents, antimycobacterial agents, antineoplastic agents, antiosteoporosis agents, antipathogen agents, antiprotozoal agents, adhesion molecules, antipyretics, antirheumatic agents, antiseptics, antithyroid agents, antiulcer agents, antiviral agents, anxiolytic sedatives, astringents, beta-adrenoceptor blocking agents, biocides, blood clotting factors, calcitonin, cardiotonics, chemotherapeutics, cholesterol lowering agents, cofactors, corticosteroids, cough suppressants, cytokines, diuretics, dopaminergics, estrogen receptor modulators, enzymes and cofactors thereof, enzyme inhibitors, growth differentiation factors, growth factors, hematological agents, hematopoietics, hemoglobin modifiers, hemostatics, hormones and hormone analogs, hypnotics, hypotensive diuretics, immunological agents, immunostimulants, immunosuppressants, inhibitors, ligands, lipid regulating agents, lymphokines, muscarinics, muscle relaxants, neural blocking agents, neurotropic agents, parasympathomimetics, parathyroid hormone, promoters, prostaglandins, psychotherapeutic agents, psychotropic agents, radio-pharmaceuticals, receptors, sedatives, sex hormones, sterilants, stimulants, thrombopoietics, trophic factors, sympathomimetics, thyroid agents, vaccines, vasodilators, vitamins, xanthines, as well as conjugates, complexes, precursors, and metabolites thereof. The active agent may be used individually or in combinations of two or more thereof. In one example, the active agent is a prophylactic and/or therapeutic agent that includes, but is not limited to, peptides, carbohydrates, nucleic acids, other compounds, precursors and derivatives thereof, and combinations of two or more thereof. In one aspect, the active agent is a pharmaceutical agent that is conventionally referred to as a small molecule.

The active agent may be a bioactive active agent, for example, a bioactive macromolecule, such as a protein (including the proteinaceous compounds described above), a polypeptide, a carbohydrate, a polynucleotide, a vector (e.g., a virus or viral particle), or a nucleic acid, or a combination of two or more thereof. The macromolecule can be natural or synthetic. Exemplary proteins include monoclonal antibodies and polyclonal antibodies. The protein can also be any known therapeutic proteins isolated from natural sources or produced by synthetic or recombinant methods. Examples of therapeutic proteins include, but are not limited to, proteins of the blood clotting cascade (e.g., Factor VII, Factor VIII, Factor IX, et al.), subtilisin, ovalbumin, alpha-1-antitrypsin (AAT), DNase, superoxide dismutase (SOD), lysozyme, ribonuclease, hyaluronidase, collagenase, growth hormone, erythropoietin, insulin-like growth factors or their analogs, interferons, glatiramer, granulocyte-macrophage colony-stimulating factor, granulocyte colony-stimulating factor, antibodies, PEGylated proteins, glycosylated or hyperglycosylated proteins, desmopressin, LHRH agonists such as: leuprolide, goserelin, nafarelin, buserelin; LHRH antagonists, vasopressin, cyclosporine, calcitonin, parathyroid hormone, parathyroid hormone peptides and insulin.

The active agent may be a cosmetic agent. Non-limiting examples of cosmetic agents include emollients, humectants, free radical inhibitors, anti-inflammatory agents, vitamins, depigmenting agents, anti-acne agents, antiseborrhoeics, keratolytics, slimming agents, skin coloring agents, and sunscreen agents. Non-limiting compounds useful as cosmetic agents include linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol, and stearyl glycerate. The cosmetic agents may be commercially available and/or prepared by known techniques. As above, the various active agents may be used individually or in combinations of two or more thereof.

The active agent may be a nutritional supplement. Non-limiting examples of nutritional supplements include proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements may be commercially available and/or prepared by known techniques. As above, the various active agents may be used individually or in combinations of two or more thereof.

The active agent may be a compound having a molecular weight of 2 kDa or less. Non-limiting examples of such compounds include steroids, beta-agonists, anti-microbial agents, antifungal agents, taxanes (antimitotic and antimicrotubule agents), amino acids, aliphatic compounds, aromatic compounds, and urea compounds. Active agents conventionally known as small molecules (or small organic molecules) are representative active agents having a molecular weight of 2 kDa or less.

The active agent may also be a diagnostic agent. Non-limiting diagnostic agents include x-ray imaging agents and contrast media. Non-limiting examples of x-ray imaging agents include ethyl 3,5-diacetamido-2,4,6-triiodobenzoate (WIN-8883, ethyl ester of diatrazoic acid); 6-ethoxy-6-oxo-hexyl-3,5-bis(acetamido)-2,4,6-triiodobenzoate (WIN 67722); ethyl-2-(3,5-bis(acetamido)-2,4,6-triiodobenzoyloxy)-butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy-acetamide (WIN 65312); isopropyl 2-(3,5-bis(acetamido)-2,4,6-triiodobenzoyloxy) acetamide (WIN 12855); diethyl 2-(3,5-bis(acetamido)-2,4, 6-triiodobenzoyloxymalonate (WIN 67721); ethyl 2-(3,5-bis (acetamido)-2,4,6-triiodobenzoyloxy)phenyl-acetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate)ester (WIN 68209). Preferred contrast agents desirably disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others maybe preferred.

In one specific embodiment, the active agent may be a therapeutic agent for prevention and/or treatment of pulmonary disorders. Non-limiting examples of such agents include steroids, beta-agonists, anti-fungal agents, anti-microbial compounds, bronchial dialators, anti-asthmatic agents, non-steroidal anti-inflammatory agents (NSAIDS), AAT, and agents to treat cystic fibrosis. Non-limiting examples of steroids for prevention and/or treatment of pulmonary disorders include but are not limited to beclomethasone (such as beclomethasone dipropionate), fluticasone (such as fluticasone propionate), budesonide, estradiol, fludrocortisone, flucinonide, triamcinolone (such as triamcinolone acetonide), flunisolide, and salts thereof. Non-limiting examples of beta-agonists for prevention and/or treatment of pulmonary disorders include salmeterol xinafoate, formoterol fumarate, levoalbuterol, bambuterol, tulobuterol, and salts thereof. Non-limiting examples of anti-fungal agents for prevention and/or treatment of pulmonary disorders include itraconazole, fluconazole, amphotericin B, and salts thereof.

The active agents may be used in a combination of two or more thereof. Non-limiting exemplary combinations include a steroid and a beta-agonist, e.g., fluticasone propionate and salmeterol, budesonide and formoterol, etc. Many other viable therapeutically active agent combinations are well known to those of ordinary skill in the art.

Continuous Phase

The continuous phase of the multi-phasic dispersion may be non-solid, for example, a liquid phase containing one solvent or a homogeneous mixture of two or more solvents (wherein at least a first solvent is soluble in or miscible with at least a second solvent), or a multiple phase system including at least two immiscible solvents. Non-limiting examples of the solvents include aqueous fluids (e.g., water $H_2O$, $D_2O$, aqueous buffers, and other aqueous solutions), non-aqueous fluids (e.g., organic solvents, organic buffers), and combinations of two or more of the foregoing. In one aspect, the non-solid continuous phase may be substantially aqueous, for example, containing more than 10% by volume, such as 25% or more, 50% or more, or 75%, or more water. The continuous phase may be partially or completely aqueous or aqueous-miscible, aqueous-immiscible, water-soluble, or water-insoluble.

The continuous phase or the liquid phase(s) thereof may have a density at ambient temperature that is less than or equal to values such as 1.10 $g/cm^3$, 1.05 $g/cm^3$, 1.0 $g/cm^3$, 0.95 $g/cm^3$, 0.9 $g/cm^3$, 0.8 $g/cm^3$, 0.7 $g/cm^3$, 0.6 $g/cm^3$, or in a range between any two of such values. When measured at the same ambient temperature, such as 20° C. or 25° C., the continuous phase or liquid phase(s) typically have a density similar or equal to, or less than that of the dispersed phase or the microparticles therein. Most typically, the continuous phase or the liquid phase(s) have a density less than that of the microparticles.

The continuous phase may further contain one or more ingredients dissolved and/or dispersed therein including but not limited to ionic and/or non-ionic polymers, salts, ions, excess reagents, excipients (e.g., sugars, polyols, surfactants), and/or manufacturing-related compounds. Non-limiting examples of salts include ammonium acetate, ammonium bicarbonate, and other buffer salts known to one of ordinary skill in the art. Non-limiting examples of sugars include trehalose, sucrose, lactose, and other carbohydrates known to one of ordinary skill in the art. Non-limiting examples of polyols include mannitol and other sugar alcohols known to one of ordinary skill in the art. The one or more fluids and/or solutes of the continuous phase may be, independently, partially or fully aqueous-miscible, aqueous-immiscible, water-soluble, and/or water-insoluble.

The continuous phase typically contains at least one non-volatile material solubilized therein. The continuous phase, for example, the solvent thereof and/or the non-volatile material therein may be soluble in and/or miscible with non-solvent, for example, having a solubility therein at ambient temperature of 10% by weight or greater, such as equal to or greater than values such as 15%, 20%, 25%, 30%, 40%, 50%, 60%, 70%, 80%, 90%, 100%, or in a range between any two of such values. Additionally, the continuous phase, the solvent thereof and/or the non-volatile material therein may be entirely miscible with the non-solvent. Greater solubility values for the continuous phase and/or components thereof in the non-solvent are generally preferred as such greater solubilities facilitate removal of the continuous phase from the dispersions in accordance with the disclosed methods.

Non-volatile Material

As previously indicated, at least the continuous phase typically contains at least one non-volatile material, the one or more non-volatile materials being different in their chemical structures and/or compositions from that of the one or more macromolecules that form the microparticles. It should be noted that the non-volatile material may be present on/in the dispersed phase, too, for example, the non-volatile material may be trapped within pores of the microparticles and/or otherwise associated with the microparticles.

Generally, the non-volatile materials have a boiling point and/or a flash point greater than about 100° C., greater than about 150° C., and/or greater than about 200° C. The non-volatile materials can be natural, synthetic, semi-synthetic, or recombinant. The one or more non-volatile materials are typically non-ionic polymers which can be independently hydrophilic, amphiphilic, aqueous-soluble (e.g., water-soluble), and/or aqueous-miscible (e.g., water-miscible), but of course, other non-volatile materials including ionic polymers and salts of non-ionic materials may also be used. The one or more non-volatile materials can beneficially independently or collectively reduce the solubility of one or more macromolecules in the continuous phase (and thus of the microparticles formed therefrom), or in the one or more solvents therein. The one or more non-volatile materials, when present in the continuous phase, typically do not covalently and/or ionically interact with, or denature, the one or more macromolecules in the microparticles. Additionally, the one or more non-volatile materials, when present in the continuous phase, typically do not complex, conjugate, aggregate, and/or agglomerate with each other, or otherwise come together, such as via covalent, ionic, and/or other interactions. Further, the one or more non-volatile materials in the continuous phase typically do not undergo gelation (e.g., form a hydrogel), either by themselves or with other ingredients present in the continuous phase. The one or more non-volatile materials independently generally have molecular weights greater than or equal to values such as 200 daltons, 300 daltons, 400 daltons, 600 daltons, 800 daltons, 1,000 daltons, 1,500 daltons, 2,000 daltons, 2,500 daltons, 3,000 daltons, 3,500 daltons, 4,000 daltons, 5,000 daltons, 8,000 daltons, and 10,000 daltons, or up to about 3,000 kilodaltons (kd), or in a range between any two of such values, for example, between 200 daltons and 10,000 daltons, between 200 daltons and 800 daltons, between 1000 daltons and 1500 daltons, between 1000 daltons and 2,000 daltons, between 1000 daltons and 2,500 daltons, between 1000 daltons and 3,000 daltons, between 1000 daltons and 3,500 daltons, between 1000 daltons and 4,000 daltons, between 1000 daltons and 5,000 daltons, between 1000 daltons and 8,000 daltons, between 1000 daltons and 10,000 daltons, between 1,500 daltons and 2,000 daltons, between 1,500 daltons and 2,500 daltons, between 1,500 daltons and 3,000 daltons, between 1,500 daltons and 3,500 daltons, between 1,500 daltons and 4,000 daltons, between 1,500 daltons and 5,000 daltons, between 1,500 daltons and 8,000 daltons, between 1,500 daltons and 10,000 daltons, between 2,000 daltons and 2,500 daltons, between 2,000 daltons and 3,000 daltons, between 2,000 daltons and 3,500 daltons, between 2,000 daltons and 4,000 daltons, between 2,000 daltons and 5,000 daltons, between 2,000 daltons and 8,000 daltons, between 2,000 daltons and 10,000 daltons, etc.

Non-limiting examples of non-volatile materials for the continuous phase include the non-ionic water-soluble and/or water-miscible polymers disclosed in U.S. Pat. Nos. 5,525, 519, 5,554,730, 5,578,709, 5,599,719, 5,981,719, 6,090,925, 6,268,053, and 6,458, 387, U.S. Publication Nos. 20030059474, 20030064033, 20040043077, 20050048127, 20050142201, 20050142205, 20050142206, 20050147687, 20050170005, 20050233945, 20060018971, 20060024240, 20060024379, 20060260777, 20070092452, 20070207210, and 20070281031, the disclosures of which are herein incorporated by reference in their entirety. The non-volatile material(s) are typically non-ionic, and can be hydrophilic, amphiphilic, aqueous-soluble, aqueous-miscible, and/or soluble or miscible in an aqueous-soluble or aqueous-miscible fluid at a temperature of 40° C. or below. Non-limiting examples of suitable non-volatile materials may be linear, branched, or cyclic, and include non-ionic polyethers, non-ionic copolyethers, non-ionic polyesters, non-ionic copolyesters, non-ionic polyether-polyester copolymers, non-ionic vinyl polymers, non-ionic pyrrolidone-containing polymers, non-ionic polymeric carbohydrates, derivatives and salts thereof, and combinations of two or more thereof. Non-limiting examples of non-ionic polyethers and non-ionic copolyethers (including copolymers and terpolymers) include but are not limited to hydroxy-terminated polyethers (e.g., polyether alcohols, polyether polyols, ethylene oxide end-capped polyethers other than polyethylene glycols) and alkyl (e.g., methyl, ethyl, propyl, butyl, etc.) end-capped derivatives thereof, such as polyalkylene glycols (e.g., poly-oxy-1,2-alkylene glycols like polyethylene glycols and polypropylene glycols, as well as polytrimethylene ether glycols and polytetramethylene ether glycols), hydroxy-terminated copolyethers (e.g., copolyether alcohols, copolyether polyols, ethylene oxide end-capped copolyethers) and alkyl (e.g., methyl, ethyl, propyl, butyl, etc.) end-capped derivatives thereof, such as block copolyethers of two or more different 1,2-alkylene oxides (e.g., polyoxyethylene-polyoxypropylene copolymers like poloxamers) and copolyethers of one or more 1,2-alkylene oxides and one or more of tetrahydrofuran, tetrahydropyran, and 1,3-propanediol (e.g., (polyethylene glycol)-(polytrimethylene ether glycol) copolymers, (polyethylene glycol)-(polytetramethylene ether glycol) copolymers). Non-limiting examples of non-ionic polyesters and non-ionic copolyesters (including copolymers and terpolymers) include hydroxy-terminated polyesters (e.g., polyester polyols, copolyester polyols, ethylene oxide end-capped or polyoxyethylene-terminated polyesters, and certain silicone polyesters, such as the likes of polyoxyethylene glycerin dicarboxylic acid esters, polyoxyethylenesorbitol dicarboxylic acid esters, polyoxyethylene glycol dicarboxylic acid esters, and polyoxyethylenealkyl esters. Non-limiting examples of non-ionic polyether-polyester copolymers (including terpolymers) include but are not limited to block copolymers of one or more lactones and/or dicarboxylic acids and one or more 1,2-alkylene oxides), esterification derivatives of the non-ionic polyethers and non-ionic copolyethers disclosed herein, and etherification derivatives of the non-ionic polyesters and non-ionic copolyesters disclosed herein, such as (polyethylene glycol)-polycaprolactone block copolymers. Non-limiting examples of non-ionic vinyl polymers (including copolymers and teipolymers) and pyrrolidone-containing non-ionic polymers (including copolymers and terpolymers) include but are not limited to polyvinyl alcohols, homopolymers and copolymers (including terpolymers) of hydroxyalkyl (alk)acrylates (e.g., hydroxyethyl acrylate, hydroxypropyl acrylate, hydroxyethyl methacrylate, hydroxypropyl methacrylate), oligo-oxyalkylene (alk) acrylates (e.g., oligo-oxyethylene acrylates, oligo-oxyethylene methacrylates), and/or alkyl end-capped oligo-oxyalkylene (alk)acrylates (e.g., methyl-capped), polyvinylpyrrolines, and (alkenyl pyrrolidone)-containing homopolymers and copolymers.

Non-limiting examples of non-ionic polymeric (including oligomeric) carbohydrates (having a molecular weight of 200 daltons to 5,000,000 daltons, such as 500 daltons, 1,000 daltons, 3,000 daltons, 5,000 daltons, 10,000 daltons, 30,000 daltons, 50,000 daltons, 100,000 daltons, 300,000 daltons, 500,000 daltons, 1,000,000 daltons, or 3,000,000 daltons, or in a range between any two of such values) and derivatives thereof include but are not limited to starch, amylopectin (branched polysaccharides), amylose (linear polysaccharides), cellulose, guar gum, guar polysaccharides, xanthan gum, dextrins (e.g, cyclodextrins, maltodextrins), dextrans, polydextroses, gellan gum, pullulan, cellodextrins, beta-glucans, and derivatives thereof, for example, non-ionic esters formed by esterification, including but not limited to benzoates and alkanoates such as acetates, propionates, butyrates, and hexanoates; or non-ionic ethers formed by etherification such as non-ionic starch ethers, non-ionic amylopectin ethers, non-ionic amylose ethers, non-ionic cellulose ethers, non-ionic guar ethers, non-ionic starch esters, non-ionic amylopectin esters, non-ionic amylose esters, non-ionic cellulose esters, non-ionic starch ether esters, non-ionic starch ester ethers, non-ionic cellulose ether esters, and non-ionic cellulose ester ethers. Non-limiting examples of non-ionic starch ethers include alkylstarches such as methylstarches, ethylstarches, propylstarches, and butylstarches; hydroxyalkyl starches such as hydroxyethyl starches (e.g., tetrastarch, pentastarch, hetastarch), hydroxypropyl starches, hydroxybutyl starches, and hydroxypentyl starches; as well as alkylhydroxyalkyl starches such as methylhydroxyethyl starches, methylhydroxypropyl starches, and ethylhydroxypropyl starches. Non-limiting examples of non-ionic amylopectin ethers and non-ionic amylose ethers include hydroxyethyl amylopectins, hydroxypropyl amylopectins, hydroxyethyl amyloses, and hydroxypropyl amyloses. Non-limiting examples of non-ionic cellulose ethers include alkylcelluloses such as methylcelluloses, ethylcelluloses, propylcelluloses, isopropylcelluloses, and butylcelluloses; hydroxyalkyl celluloses such as hydroxyethyl celluloses, hydroxypropyl celluloses, hydroxyisopropyl celluloses, hydroxybutyl celluloses, and hydroxypentyl celluloses; as well as alkylhydroxylalkyl celluloses such as methylhydroxyethyl celluloses, methylhydroxypropyl celluloses, methylhydroxybutyl celluloses, ethylhydroxyethyl celluloses, ethylhydroxypropyl celluloses, propylhydroxyethyl celluloses, propylhydroxypropyl celluloses, isopropylhydroxypropyl celluloses, butylhydroxypropyl celluloses, pentylhydroxypropyl celluloses, and hexylhydroxypropyl celluloses. Non-limiting examples of non-ionic guar ethers include alkylguar polysaccharides such as methylguar polysaccharides, ethylguar polysaccharides, propylguar polysaccharides, and butylguar polysaccharides; hydroxyalkylguar polysaccharides such as hydroxyethylguar polysaccharides, and hydroxypropylguar polysaccharides; as well as alkylhydroxylalkylguar polysaccharides such as methylhydroxyethylguar polysaccharides, methylhydroxypropylguar polysaccharides, ethylhydroxypropylguar polysaccharides. Other non-ionic polymeric carbohydrates include methyl cellulose, hydroxyethyl cellulose, hydroxyethyl methylcellulose, hydroxypropyl methylcellulose, ethylhydroxyethyl cellulose, methylethylhydroxyethyl cellulose, butylglycidyletherhydroxyethyl cellulose, laurylglycidyletherhydroxyethyl cellulose, hydroxymethylhydroxyethyl cellulose, butylglycidylether modified hydroxyethyl cellulose, methylhydroxyethylcellulose, methylhydroxypropyl cellulose, starch esters (e.g. alkyl succinic anhydride modified starchstarch acetates and starch alkenylsuccinates), cellulose esters (cellulose monobutyrates and monopropionates), cellulose ether esters (hydroxyalkyl cellulose-2-hydroxycarboxylic acid esters), poly(3-hydroxyoxetane)s. Non-limiting examples of non-ionic polymeric carbohydrate esters include those having a degree of substitution ranging from 0.5 to 1.0, such as from 0.7 to 0.9, and are water-soluble. Ionic salts of the foregoing non-ionic materials, if capable of being made, may also be used. For example, salts of polysaccharides such as dextran sulfate, dextrin sulfate, and sodium alginate, can also be used.

Dispersed Phase

The dispersed phase of the multi-phasic dispersion may comprise solid microparticles. Typically, it is preferred that the microparticles are substantially insoluble in and/or substantially immiscible with the non-solvent, for example, having a solubility therein at ambient temperature of less than 10% by weight, such as 5 wt. % or less, 3 wt. % or less, 1 wt. % or less, 0.5 wt. % or less, 0.1 wt. % or less, 0.05 wt. % or less, 0.01 wt. % or less, or in a range between any two of such values.

The dispersed phase may further include other materials in association with the solid microparticles, for example, a non-volatile material, salt, or excipient added during microparticle formation. Generally, such materials are not desired in the isolated microparticles and are therefore desirably removed from the dispersion. Accordingly, it is desirable for such materials to have greater solubilities in the non-solvent.

Nonsolvent

The non-solvent generally is not limited as long as only relatively insignificant amounts of the microparticles are capable of being dissolved therein. Thus, the dispersed phase or at least the microparticles thereof are preferably substantially insoluble in the non-solvent. Accordingly, only small amounts of microparticles are dissolved by the nonsolvent as the microparticles migrate into or through (and hence at least transitorily dispersed) in the non-solvent. More specifically, the microparticles usually have a solubility in the non-solvent such that no more than 5 weight percent (such as 3 wt. % or less, 1 wt. % or less, 0.5 wt. % or less, 0.1 wt. % or less, 0.05 wt. % or less, and/or 0.01 wt. % or less, or in a range between two of such values) is dissolved when the microparticles are dispersed in the non-solvent. The relatively low solubility of the microparticles in the non-solvent has been found to advantageously reduce the amount of microparticle aggregate formation observed in the collected microparticles relative to previous methods for processing microparticles where the microparticles were processed or collected directly in/from the continuous phase of the original dispersion.

The non-solvent may comprise a single non-solvent component alone or a combination of two or more thereof. Generally, at least one component or a portion (e.g., a layer) of the non-solvent has a density ($D_n$) greater than or substantially equal to that of the continuous phase ($D_c$). Typically, the non-solvent components have a density $D_n$ less than that of the microparticles ($D_p$). When the density of the microparticles $D_p$ is greater than that of the continuous phase $D_c$, and greater than or approximately the same as the non-solvent $D_n$, it is possible to utilize centrifugation to selectively effect migration of the microparticles into or through the non-solvent, as described in further detail below. Methods using electrophoresis are not similarly limited as the direction of the applied electric field can be controlled to selectively effect migration of the microparticles independently of the density values of the microparticles, the continuous phase, and the non-solvent, as described in further detail below.

In some embodiments, the non-solvent may comprise a density gradient formed, by example, by gently overlaying layers of lower concentrations of a non-volatile material on layers of higher concentrations of the non-volatile material.

Furthermore, in alternative embodiments, at least one component of the non-solvent may have a viscosity greater than that of the continuous phase of the original dispersion (in addition to or instead of having a density greater than that of the continuous phase).

The non-solvent may contain one or more non-volatile materials solubilized therein. Representative non-volatile materials include those disclosed above for use in the continuous phase. The non-volatile materials of the nonsolvent may be independent of (e.g., the same as or different from, such as in chemical structure and/or molecular weight) those contained within the original dispersion. Lower molecular weight non-volatile materials (at least relative to the non-volatile materials present in the continuous phase) are generally preferred for use in/as the non-solvent because such materials are easier to remove, for example, such materials can be removed using super critical fluid extraction with carbon dioxide alone or in combination with a co-solvent such as ethanol. Lower molecular weight PEGs having molecular weights less than 1000 daltons such as PEG 300 are particularly useful in this regard. In one particular embodiment, the non-solvent may be selected from liquid polyethylene glycols or liquid poloxamers, or combinations of two or more thereof Aqueous solutions containing one or more water-soluble non-ionic polymers solubilized therein may also be used as the non-solvent.

The non-solvent can comprise one or more aqueous liquids, non-aqueous liquids, or combinations of two or more thereof (in place of or in addition to the one or more non-volatile materials). The non-solvent may further contain stabilizers, salts, antioxidants, and combinations of two or more thereof.

The aqueous liquids useful for the non-solvent include $H_2O$, $D_2O$, aqueous buffers, and any other aqueous solutions. Suitable aqueous solutions may contain solubilized solutes including but not limited to buffer salts having ammonium, $Na^+$, and $K^+$ as cations and/or acetate and bicarbonate as anions, other salts including but not limited to NaCl, stabilizers (e.g., histidine and salts thereof), antioxidants (e.g., EDTA), sugars (e.g., sucrose, trehalose, lactose, maltose), density gradient materials (e.g., salts of alkali metals such as NaCl, NaBr, NaI, KBr, CsF, CsCl, CsBr, cesium sulfate, cesium acetate, cesium trifluoroacetate, RbCl, and potassium tartrate; neutral, water-soluble molecules such as sucrose with optional addition of glucose; glycerol; mineral oil; hydrophilic macromolecules such as dextran, sucrose-epichlorohydrin copolymer, and bovine serum albumin; other synthetic molecules such as sodium or methyl glucamine salts of triiodobenzoic acid and metrizoic acid; and metrizamides), polyols, surfactants, excipients, and combinations of two or more thereof. Materials and techniques for density gradient centrifugation are described in "Centrifugation in Density Gradients," C. A. Price, Academic Press, New York, 1982. Standard methods involving density-gradient techniques include ASTM D1505-03, ASTM D1505-98, and ISO 1183-2.

The non-aqueous liquids useful for the non-solvent include polar aprotic (or dipolar aprotic) organic liquids such as ketones, nitriles, esters, aldehydes, N,N-dimethylformamide; nonpolar aprotic organic liquids such as ethers (e.g., methoxylated ethers, alkylated ethers, diether, triethers, cyclic ethers, crown ethers); and tertiary organic liquids such as tertiary alcohols, tertiary acids, tertiary amides. Specific representrative organic liquids useful in the non-solvent include 2-methyl-2-propanol, 2-dimethyl-2-butanol, 3-methyl-3-heptanol, t-amyl alcohol, glycerin, N,N-dimethylformamide (DMF), dimethylsulfoxide (DMSO), acetone, acetonitrile, ethyl acetate, isopropyl acetate, butyl acetate, propyl acetate, carbonates (e.g., dimethyl carbonate, ethyl methyl carbonate, diethyl carbonate, ethyl propyl carbonate, dipropyl carbonate, and isomers thereof), cyclic carbonates (e.g., ethylene carbonate, propylene carbonate, butylene carbonate, pentylene carbonate, and isomers thereof), hexamethylphosphoric triamide (HMPA), tetrahydrofuran (THF), N,N-dimethylacetamide, N-methyl-2-pyrrolidone, tetramethyl urea, dioxane, dichloromethane, 1,2-dichloroethane, dimethoxyethane, diethylene glycol dimethyl ether, diisopropyl ether, glycofurol, hydrocarbons (linear, branched, or cyclic) such as pentane, hexane, heptane, cyclohexane, toluene or xylene, methyl ethyl ketone, isobutyl methyl ketone, menthol, thymol, camphor, imidazole, coumarin, dimethylsulfone, urea, vanillin, camphene, salicylamide, pyridine, 2-aminopyridine, pyrimidine, piperidine, and combinations of two or more thereof.

Additional non-aqueous liquids useful for the non-solvent include aqueous-miscible organic liquids such as acetyl tributyl citrate, acetyl triethyl citrate, benzyl alcohol, butyrolactone, caprolactam, decylmethylsulfoxide, diacetin, diethyl phthalate, diethyl tartrate, diethylene glycol dimethyl ether, dimethoxyethane, dimethylethylamide, dimethylformamide, dimethylsulfoxide, 1-dodecylazacyclo-heptan-2-one, ethanol, ethyl acetate, ethyl lactate, ethylene carbonate, ethylene glycol, ethylene oxide, glycerine, glycerol formal, glycofurol (also referred to as "tetraglycol" or "tetrahydrofurfuryl alcohol polyethyleneglycol ether"), isopropanol, methanol, methyl acetate, methyl ethyl ketone, 2-methyl-2-propanol, N-methyl-2-pyrrolidone, octanol, polysorbates (e.g., 20, 40, 60, 65, 80), propylene carbonate, propylene glycol, propylene oxide, 2-pyrrolidone, silicone fluid, tetraethyleneglycol, tetrahydrofuran, triacetin, tributyl citrate, tributyrin, triethyl citrate, triethyl phosphate, and combinations of two or more thereof. In one particular example, the non-solvent may contain one or more of liquid PEGs, liquid poloxamers, glycofurol, tetraethylene glycol, water and/or aqueous buffer, and an alcohol.

Further examples of non-aqueous liquids useful for the non-solvent include halogenated liquids. Non-limiting examples of halogenated liquids include partially halogenated (fluorinated, chlorinated, brominated, and/or iodinated) and perhalogenated (perfluorinated, perchlorinated, perbrominated, periodinated) derivatives of the organic liquids disclosed herein (such as trichloro-t-butanol, perfluoro-t-butanol), chlorocarbons, chlorohydrocarbons, perchlorocarbons, perchloroalkanes, hydrochloroethers, fluorocarbons, fluorohydrocarbons, perfluorocarbons, perfluoroalkanes, hydrofluoroethers, bromocarbons, bromohydrocarbons, chlorofluorocarbons, hydrochlorofluorocarbons, chloroperfluorocarbons, hydrochlorofluoroethers, and mixtures of two or more thereof.

When used in centrifugation methods, the non-solvent preferably has a volatility similar to or greater than that of water and a density greater than that of water. Thus, the non-solvent or at least one non-aqueous liquid therein may have a boiling point of less than or equal to 100° C. and a density greater than 1 g/cm$^3$. Non-limiting examples of non-aqueous liquids having a volatility similar to or greater than that of water and a density greater than that of water include carbon disulfide, lactic acid, certain chlorofluorocarbons (e.g., 1,1,2-trichlorotrifluoroethane, trichlorofluoromethane), certain hydrochlorofluorocarbons (such as dichlorofluoromethane), certain perfluorocarbons (e.g., perfluoropentane, perfluorohexane, perfluoroheptane, perfluoro-N-methylmorpholine), certain perfluoroethers (such as perfluoro-2-butyltetrahydrofuran), and certain hydrofluoroethers.

Certain non-limiting liquids suitable for the non-solvent and their characteristics are listed in Table 1 below.

TABLE 1

| Liquid | Density$^a$ | BP$^b$ | FP$^c$ | Sol.$^d$ | LD$_{50}$$^e$ | VP$^f$ |
|---|---|---|---|---|---|---|
| acetic acid | 1.05 | 118 | 16.6 | $^i$M | 3.3 | 2.11 |
| carbon tetrachloride | 1.59 | 76.7 | −22.4 | 0.05 | 2.3 | 15. |
| Chloroform | 1.50 | 61.2 | −63.5 | 0.8 | 0.7 | 25.9 |
| diethylene glycol | 1.12 | 245 | −10 | M | 13 | <0.01 |
| DMSO | 1.09 | 189 | 18.4 | M | 18 | 0.08 |
| ethylene glycol | 1.12 | 197 | −13 | M | 4.7 | <0.01 |
| Glycerol | 1.26 | 290 | 17.8 | M | 13 | <0.01 |
| methylene chloride | 1.32 | 39.8 | −96.7 | 1.32 | 1.6 | 46.7 |
| heavy water, D$_2$O | 1.11 | 101.3 | 4 | M | NT | 2.19 |
| Perfluorohexane | 1.68 | 59 | −4 | 10 ppm | 5 | 23.6 |
| 1,1,1-trifluorotoluene | 1.189 | 103 | −29 | | 15 | 42.8 |
| CFCl$_3$ | 1.49 | 24 | −111 | 0.11 | 0.45 | 0.013 |
| carbon disulfide | 1.27 | 46 | −112 | <1% | 3.2 | |
| Nitromethane | 1.138 | 101 | −29 | | | |
| ethylene carbonate | 1.321 | 243 | 35 | M | 10 | 0.02 |

TABLE 1-continued

| Liquid | Density[a] | BP[b] | FP[c] | Sol.[d] | LD$_{50}$[e] | VP[f] |
|---|---|---|---|---|---|---|
| Sulfolane | 1.262 | 287 | 28.5 | M | 1.94 | |
| propylene carbonate | 1.189 | 240 | −55 | 23% | 29 | |
| trifluoroacetic acid (TFA) | 1.489 | 72 | −15 | M | 0.5 | |
| 2,2,2-trifluoroethanol | 1.393 | 79 | −44 | | 0.24 | |
| formic acid | 1.22 | 101 | 8.3 | M | 1.21 | |
| Formamide | 1.133 | 211 | 2.6 | | 5.5 | |
| propylene glycol | 1.04 | 188.2 | −60 | M | 22 | |
| trimethylene glycol | 1.05 | 214.4 | −26.7 | M | 4.77 | |
| propylene glycol monophenyl ether | 1.063 | 242.7 | 12.78 | 1.1 | 2.83 | |
| diphenyl ether | 1.066 | 258 | 26.87 | | 3.37 | |
| ethylene glycol monobenzyl ether | 1.07 | 265 | | 4 | 1.19 | |
| diethyl oxalate | 1.08 | 185.4 | −40.6 | | 0.4 | |
| lactic acid, methyl ester | 1.09 | 145 | | decomp | 2 | |
| triethylene glycol | 1.119 | 287.4 | −7.2 | M | 17 | |
| gamma-butyrolactone | 1.125 | 204 | −44 | M | 1.54 | |
| furfuryl alcohol | 1.1285 | 171 | −29 | M | 0.275 | |
| tetraethylene glycol | 1.13 | 327.3 | −4 | M | 29 | |
| Furfural | 1.1545 | 161.8 | −36.5 | | 0.05 | |
| Trioxane | 1.17 | 114.5 | 64 | soluble | 3.2 | 1.73 |
| lactic acid | 1.206 | 83.5 | 18 | M | 3.7, 3.5 | 2.53 |
| 1,1,1-trichloroethane | 1.32 | 74.1 | −30.4 | 0.15 | 9.6 | |
| dichlorofluoromethane | 1.366 | 8.9 | −135 | | NT | 181 |
| 1,2-dichlorotetrafluoroethane | 1.455 | 4.1 | −94 | 0.13 | 2.25 | |
| trichlorofluoromethane | 1.476 | 23.63 | −110.5 | 0.11 | NT | |
| methanesulfonic acid | 1.48 | 167 | 20 | | 0.2 | |
| 1,1,2-trichloroethylene | 1.5, 1.44 | 86.7 | −84.8 | 0.11 | 2.4 | |
| pentafluoropropyl alcohol | 1.51 | 80 | | soluble | 1 | |
| 1,1,2-trichlorotrifluoroethane | 1.564 | 47.63 | −36.4 | 0.017 | 43 | |
| dibutyl phthalate | | | | | | |
| N-methylpyrrolidone | 1.03 | 202 | −25 | 100% | 4.15 | |
| lactic acid, ethyl ester | | | | | | |
| tetrahydropyran-2-methanol | | | | | | |
| 1,4-dioxane | | | | | | |
| diethylene glycol methyl ether | 1.02 | 194 | | 100% | | |
| Ethylene glycol methyl ether acetate | | | | | | |
| diethylene glycol monoethyl ether acetate | | | | | | |
| 1,3-butanediol | | | | | | |
| 1-methoxy-2-propanol | | | | | | |
| Perfluoropentane, $C_5F_{12}$ | 1.65 | 30 | | | | |
| perfluoro-N-methylmorpholine | 1.71 | 50 | | | | |
| Perfluorohexane | 1.67 | 56 | | 0.03 | 5 | |
| Perfluoroheptane, $C_7F_{16}$ | 1.73 | 77-87 | | | | |
| perfluorooctane, $C_8F_{18}$ | 1.76 | 101 | | I | | |
| perfluorotripropylamine, perfluamine, $C_9F_{21}N$ | 1.82 | 128 | | | | |
| perfluoro-N,N,N',N'-tetrapropylhexanediamine | 1.9 | 254 | | | | |
| [g]Fluorinert ® FC-40, mixture of perfluorotributylamine & perfluorodibutylmethylamine | 1.85 | 155 | −57 | 7 ppm | NTO | 0.43 |
| Fluorinert ® FC-43, $C_{12}F_{27}N$, perfluorotributylamine, | 1.86 | 174 | −50 | 7 ppm | 10 | 0.19 |
| Fluorinert ® FC-70, $C_{15}F_{33}N$, perfluorotriamylamine, | 1.94 | 215 | −25 | 8 ppm | NTO | 0.015 |
| Fluorinert ® FC-71 | 2 | 253 | | | | 0.027 |
| Fluorinert ® FC-72 | 1.68 | 56 | −90 | 10 ppm | NTO | 30.9 |
| Fluorinert ® FC-75, $C_8$ perfluoro compounds like $C_8F_{16}O$, perfluoro-2-butyltetrahydrofuran | 1.8 | 102 | −88 | | | 4.13 |
| Fluorinert ™ FC-77 | 1.78 | 97 | −110 | 13 ppm | | 5.62 |
| Fluorinert ™ FC-84 | 1.73 | 80 | −95 | 11 ppm | | 10.6 |
| Fluorinert ™ FC-87 | 1.65 | 30 | −115 | 7 ppm | | 81.1 |
| Fluorinert ™ FC-104 | 1.76 | 101 | −65 | 11 ppm | | 3.87 |
| Fluorad ™ FC-722 | 1.7 | 56 | | | | 30.9 |
| Fluorinert ™ FC-3255 | 1.77 | 103 | −30 | 11 ppm | | 4.15 |
| Fluorinert ™ FC-3283 | 1.82 | 128 | −50 | 7 ppm | NTO | 1.44 |
| Fluorinert ™ FC-3284 | 1.71 | 50 | −73 | 14 ppm | NTO | 35.7 |
| Fluorinert ™ FC-5311, tetra-cosafluorotetraphenanthrene | 2 | 215 | | | | 0.015 |
| Fluorinert ™ FC-5312, $C_{15}$ perfluorocompounds | 1.94 | 215 | −25 | 8 ppm | | 0.015 |
| [g]PF-5050 | 1.63 | 30 | −115 | 14 ppm | | |
| PF-5052 | 1.7 | 50 | −80 | 14 ppm | | 81.1 |

TABLE 1-continued

| Liquid | Density[a] | BP[b] | FP[c] | Sol.[d] | LD$_{50}$[e] | VP[f] |
|---|---|---|---|---|---|---|
| PF-5056 | 1.8 | 25-80 | | <15 ppm | | |
| PF-5058 | 1.75 | 80-100 | | <15 ppm | | |
| PF-5060 & PF-5060DL, C$_6$F$_{14}$ | 1.68 | 56 | −90 | 10 ppm | >5 | |
| PF-5070, C$_7$F$_{16}$ | 1.73 | 80 | −95 | 11 ppm | | |
| PF-5080, C$_8$F$_{18}$ | 1.77 | 101 | −30 | 11 ppm | >5 | |
| PFG-3480, C$_4$F$_8$O, octafluorotetrahydrofuran | 1.52 | 0.8 | −83 | | | |
| [g]Novec ™ HFE-7000, 3M engineered fluids, hydrofluoroethers, 1-methoxyheptafluoropropane | 1.4 | 34 | −122.5 | 60 ppm | >2 | 64.6 |
| Novec ™ HFE-7100, methoxynonafluorobutane | 1.51 | 60 | −135 | 95 ppm | >5 | 26.8 |
| Novec ™ HFE-71DE, 50% C$_4$F$_9$OCH$_3$ & 50% t-DCE | 1.37 | 41 | −24 | 324 ppm | 21 | 51.1 |
| Novec ™ HFE-71DA, 52.7% C$_4$F$_9$OCH$_3$, 44.6% t-DCE, & 2.7% ethanol | 1.33 | 40 | −29 | | | |
| Novec ™ HFE-71IPA, 95.5% C$_4$F$_9$OCH$_3$ & 4.5% isopropanol | 1.48 | 55 | −42 | | | |
| Novec ™ HFE-7200, ethoxynonafluorobutane | 1.42 | 76 | −138 | 92 ppm | >5 | 15.7 |
| Novec ™ HFE-72DE, blend of 10% C$_4$F$_9$OCH$_3$, 20% C$_4$F$_9$OC$_2$H$_5$, & 70% t-DCE | 1.28 | 43 | | 360 ppm | >100, >92, 24 | |
| Novec ™ HFE-72DA, blend of 10% C$_4$F$_9$OCH$_3$, 20% C$_4$F$_9$OC$_2$H$_5$, 68% t-DCE, & 2% isopropanol | 1.27 | 44 | −138 | | | 48.0 |
| Novec ™ HFE-7500, 2-trifluoromethyl-3-ethoxydodecafluorohexane | 1.61 | 130 | −110 | 45 ppm | >2 | 2.1 |
| Novec ™ HFE-8200 | 1.43 | 76 | −138 | 92 ppm | >5 | |
| Novec ™ 1230 dodecafluoro-2-methylpentan-3-one | 1.6 | 49.2 | −108 | | >100 I | |
| [g]HFC-4310, C$_5$H$_2$F$_{10}$ | 1.73 | 80 | −95 | 490 ppm | | |
| HFC-4310mee, C$_5$H$_2$F$_{10}$ | 1.58 | 54 | | 400 ppm | 11 I | |
| HFC-4310 azeotrope, 62% C$_5$H$_2$F$_{10}$, 38% t-DCE | 1.41 | 39 | | | | 61.9 |
| HFC-4310SMT, 52.9% C$_5$H$_2$F$_{10}$, 43% t-DCE, 4% methanol, 0.1% stabilizer | 1.37 | 37 | −10 | | | 62.8 |
| HCFC-225, C3Cl2F5H | 1.55 | 54 | −131 | 310 ppm | 37 I | 38.7 |
| [h]AK-225 AES, azeotrope of 95.5% C$_3$Cl$_2$HF$_5$ & 4.5% ethanol | 1.49 | 52 | −138 | | | 55.2 |
| n-propyl bromide, C$_3$H$_7$Br | 1.35 | 71 | −110 | 500 ppm | | |
| 1,1,1-TCA, CH$_3$CCl$_3$ | 1.32 | 74 | −39 | 170 ppm | 16 | |
| pentafluorobenzene, C$_6$F$_5$H | 1.51 | 85 | −48 | | 2 | |
| C$_7$F$_{15}$OC$_2$H$_5$ | 1.61 | 128 | −100 | | >2 | |
| [i]Galden HT-135 | 1.73 | 135 | −100 | | | |
| [j]Genetron ® HFC-134a, CF$_3$CH$_2$F | 1.21 | −26.2 | −92.5 | 0.11% | 62 I | |
| [j]Genesolv ® 2000 HFC-141b, CCl$_2$FCH$_3$ | 1.24 | 32 | −103 | 420 ppm | >5 | 75.9 |
| Genesolv ® 2004, azeotrope of 95.8% CCl$_2$FCH$_3$, 3.9% methanol & 0.3% nitromethane | 1.22 | 29.4 | | | | 70.3 |
| Genesolv ® S-F, 1,1,1,3,3-pentafluoropropane, HFC-245fa | 1.32 | 15 | −142 | 1600 ppm | >200 I | |
| Genesolv ® S-T, azeotrope of 65% SF & 35% t-DCE | 1.32 | 15.7 | −103 | | >200 I | |
| Genesolv ® S-TZ, azeotrope of 87% SF & 13% t-DCE | 1.34 | 15 | −103 | | >200 I | |
| Genesolv ® D series DSTD & DEG, CFC-113, CCl$_2$FCClF$_2$, | 1.56 | 48 | −35 | 110 ppm | 55 I | 44.1 |
| [g]Freon ® TE, azeotrope of 96% C$_2$Cl$_3$F$_3$ & 4% ethanol | 1.5 | 45 | −42 | | | 48.3 |
| PEG 200 | 1.11 | 250 | −65 to −50 | M | 28.0 | <0.01 |
| PEG 300 | 1.12 | 250 | −15 to −10 | M | 27.5 | <0.01 |
| PEG 400 | 1.125 | 250 | −6 to 8 | M | 30.2 | <0.01 |
| PEG 500 | 1.13 | 250 | | M | | <0.01 |
| PEG 540 | 1.13 | 250 | | M | | <0.01 |
| PEG 600 | 1.14 | 250 | 15-25 | M | 38.1 | <0.01 |
| Pluronic ® L-10 (MW 3200) | 1.04 | | −5 | >10% | >2 | <0.01 |
| Pluronic ® L-24 | | | | | >2 | |
| Pluronic ® L-31 (MW 1100) | 1.02 | | −32 | >10% | >2 | |
| Pluronic ® L-35 (MW 1900) | 1.06 | | 7 | >10% | >2 | |

TABLE 1-continued

| Liquid | Density[a] | BP[b] | FP[c] | Sol.[d] | LD$_{50}$[e] | VP[f] |
|---|---|---|---|---|---|---|
| Pluronic ® L-42 (MW 1630) | 1.03 | | −26 | | >2 | |
| Pluronic ® L-43 (MW 1850) | 1.04 | | −1 | >10% | >5 | |
| Pluronic ® L-44 (MW 2200) | 1.05 | | 16 | >10% | >5 | |
| Pluronic ® L-44NF (MW 2200) | 1.05 | | 16 | >10% | >5 | |
| Pluronic ® L-61 (MW 2000) | 1.01 | | −29 | <1% | >5 | |
| Pluronic ® L-62 (MW 2500) | 1.03 | | −4 | >10% | >2 | |
| Pluronic ® L-62D (MW 2360) | 1.04 | | −1 | <10% | >5 | |
| Pluronic ® L-62LF (MW 2450) | 1.03 | | −10 | >10% | 5 | |
| Pluronic ® L-63 (MW 2650) | 1.04 | | 10 | | >2 | |
| Pluronic ® L-64 (MW 2900) | 1.05 | | 16 | >10% | >2 | |
| Pluronic ® L-68 | | | | | >2 | |
| Pluronic ® L-72 (MW 2850) | 1.03 | | −7 | | >2 | |
| Pluronic ® L-81 (MW 2750) | 1.02 | | −37 | <0.1% | >2 | |
| Pluronic ® L-92 (MW 3650) | 1.03 | | 7 | <10% | >2 | |
| Pluronic ® L-101 (MW 3800) | 1.02 | | −23 | <0.1% | >5 | |
| Pluronic ® L-121 (MW 4400) | 1.01 | | 5 | <1% | >2 | |
| Pluronic ® L-122 (MW 5000) | 1.03 | | 20 | <1% | >2 | |
| Pluronic ® L-123 (MW 5750) | | | | | >2 | |
| Pluronic ® N-3 | 1.04 | | −7 | | >5 | |
| Pluronic ® 10R5 (MW 1950) | 1.06 | | 15 | >10% | >2 | |
| Pluronic ® 17R2 (MW 2150) | 1.03 | | −25 | >10% | >2 | |
| Pluronic ® 17R4 (MW 2650) | 1.05 | | 18 | >10% | >5 | |
| Pluronic ® 25R2 (MW 3100) | 1.04 | | −5 | >10% | >2 | |
| Pluronic ® 25R4 (MW 3600) | 1.05 | | 25 | >10% | >2 | |
| Tetronic ® 304 (MW 1650) | 1.06 | | −11 | >10% | >2 | |
| Tetronic ® 701 (MW 3600) | 1.02 | | −21 | <1% | >2 | |
| Tetronic ® 704 (MW 5500) | | | | | >2 | |
| Tetronic ® 901 (MW 4700) | 1.02 | | −23 | <0.1% | >2 | |
| Tetronic ® 904 (MW 6700) | 1.04 | | 29 | >10% | >2 | |
| Tetronic ® 1301 (MW 6800) | 1.02 | | −9 | <1% | >2 | |
| Tetronic ® 90R4 (MW 6900) | 1.05 | | 12 | >10% | >5 | |
| Tetronic ® 150R1 (MW 8000) | 1.01 | | −17 | <0.1% | >2 | |
| Glycofurol | 1.07 | | | >50% | 7.8 | |
| Tetraethylene glycol | 1.12 | | −5.6 | | >2 | |

[a] Density at liquid state, measured at ambient temperature such as 25° C.
[b] Boiling point (BP), ° C.
[c] Freezing/melting point (FP), ° C.
[d] Solubility (Sol) of water in the liquid, in g/100 g or ppm (parts per million by weight), at ambient temperature such as 20-25° C.
[e] LD$_{50}$, in g/kg body weight, is the minimal amount of the liquid reported in the literature that when administered to rats orally all at once (acute toxicity) causes the death of 50% of the rats being tested.
[f] Vapor pressure (VP), in kPa, at ambient temperature such as 20-25° C.
[g] Fluorinert ™, Fluorad ™, Novec ™, Performance Fluids (PF), Secondary Fluid (SF), are all available from 3M, St. Paul, MN.
[h] AK-225 series of liquid materials are available from AGC Chemicals Americas, Inc., Bayonne, NJ.
[i] Galden ® and Perfluorosolv ® series of liquids are available from Solvay Solexis, Inc., Thorofare, NJ.
[j] Genetron ® and Genesolv ® series of liquids are available from Honeywell, Morristown, NJ.
[k] Freon ® series of liquids are available from DuPont-Mitsui Fluorochemicals Co. Ltd. Tokyo, Japan.
[l] Miscible (M) with water.

Selectively Effecting Migration of the Microparticles

The methods facilitate selectively effecting migration of the microparticles into or through the non-solvent to allow the microparticles to be collected. The methods facilitate separation of a majority of the microparticles from the dispersion, for example, at least 50%, at least 60%, at least 70%, at least 80%, at least 90% of the microparticles. Non-limiting methods to achieve the migration of the microparticles include, at least in part, centrifugation, electrophoresis, and other mechanical means.

Advantageously, the microparticles can be migrated into a non-solvent that is a pharmaceutically acceptable diluent such that the microparticles can be administered to a subject without need for further processing, for example, without need for performing a drying step (e.g., lyophilization or evaporation under reduced pressure and/or increased temperature) or a subsequent reconstitution step. Avoiding these processing steps is advantageous because they are energy intensive, time-consuming, and not easily converted to continuous-flow operation. Further, lyophilization can induce denaturation and aggregation of many macromolecules such as proteins.

By using non-limiting techniques such as centrifugation, the microparticles can be migrated into or through the non-solvent to a location (e.g., within the non-solvent, at an interface between the non-solvent and its container, or beyond the non-solvent) at which the bulk of the continuous phase of the original dispersion or at least the non-volatile material therein cannot arrive, thus achieving separation of the microparticles from the original dispersion. The microparticles may be concentrated as a result of the separation process, such as by forming a band thereof in the non-solvent, or by forming a pellet thereof at the bottom and/or on the wall of the container.

Using centrifuges with fixed angle or swinging bucket rotors, the non-solvent may be placed first into the centrifuge tube through a single addition or multiple additions depending on whether a single component or multi-component non-solvent is employed. Then the dispersion may be placed into the same centrifuge tube, on top of non-solvent, without mixing the two. To prevent inadvertent, undesirable mixing, the non-solvent in the centrifuge tube may be frozen prior to the addition of the dispersion, and then thawed after the addition of the dispersion using a heating-cooling cycle. The freezing and/or thawing can be done prior to or after loading the centrifuge tube into the centrifuge rotor.

To selectively effect migration of the particles, the centrifuge may be accelerated to operating speed (e.g., 3,000×g to 20,000×g), run for a predetermined period of time (e.g., 5 min to 1 hr), and decelerated to a stop. The supernatant in the centrifuge tube, containing at least the bulk of the continuous phase of the original dispersion, may be aspirated off or otherwise decanted. It may also be possible to aspirate a bulk portion of the non-solvent. The microparticles in the form of a pellet at the bottom of the centrifuge tube or a band (e.g., isopycnic band) in the non-solvent may then be easily collected.

When using centrifuges with continuous-flow rotors (e.g., Sorvall® Contifuge®, Beckman Coulter's JCF-Z and CF-32 Ti), the non-solvent may be first pumped at a flow rate of 100 mL/min to 500 mL/min into the rotor at a low rotor speed. After operating rotor speed (e.g., 3,000×g to 20,000×g, such as 7,000×g to 10,000×g) is reached, the dispersion may be pumped into the rotor at a flow rate of 100 mL/min to 500 mL/min (e.g., 200 mL/min to 300 mL/min). The microparticles may sediment out of the flowing stream of the dispersion as a microparticle-depleted effluent containing the bulk of the continuous phase then emerges out of the rotor. After the dispersion has been completely pumped into the rotor, a suitable chaser (e.g., a buffer or water) may be pumped into the rotor to flush the lines. If the microparticles form a pellet on the rotor wall, the rotor can be decelerated to a stop position, the supernatant remaining in the rotor may be decanted, and the microparticles may be collected by scraping the pellet off the rotor wall. If the microparticles form a band (e.g., isopycnic band) in the remainder of the non-solvent, the rotor may be decelerated to a low speed. A dense solution (e.g., the same non-solvent or a portion thereof, or a different non-solvent) may be pumped into the rotor to displace the microparticle-laden non-solvent, thereby facilitating collection.

The process to separate the dispersed phase or the microparticles therein from the continuous phase or the non-ionic polymer therein may be carried out at a temperature above the freezing temperatures of the continuous phase and the non-solvent, and below the degradation temperature of the microparticles or the bioactive macromolecule therein, such as at or below ambient temperature, or above, at, or below temperatures such as 40° C., 37° C., 30° C., 25° C., 20° C., 15° C., 10° C., 5° C., 2° C., 0° C., −5° C., −10° C., −15° C., 20° C., or in a range between any two of such temperatures.

The microparticle collection may be suitable for storage (e.g., at ambient temperature or lower over 1 week to 2 years or longer) and/or administration to a human subject (e.g., injectable or otherwise deliverable with or without further dilution using the same non-solvent or other non-solvents) without drying and reconstitution. The concentration of the one or more bioactive macromolecules in the microparticle collection following the separation process may be increased to 50 g/L or greater, such as greater than or equal to 100 g/L, 150 g/L, 200 g/L, 250 g/L, 280 g/L, 300 g/L, 350 g/L, 400 g/L, 450 g/L, 500 g/L, 550 g/L, 600 g/L, or in a range between any two of such values.

Prior to the separation process, the dispersion may be concentrated using non-limiting techniques such as centrifugation and/or diafiltration. Diafiltration may be carried out at a temperature at or below ambient temperature (such as 2-8° C.). A diafiltration medium may be used to exchange and/or replace at least a portion of the continuous phase of the original dispersion. The diafiltration medium may be a non-solvent to the microparticles, such as those disclosed herein. A diafiltration apparatus known to one of ordinary skill in the art, containing a peristaltic pump, a reservoir vessel, a hollow fiber cartridge, and tubing, may be used for the concentration process. An intermediate dispersion containing the microparticles and the non-solvent may be formed through the concentration process, wherein the concentration of the one or more bioactive macromolecules therein may be elevated many fold (such as 2 folds or more, 5 fold or more, 10 folds or more, 20 folds or more, or 40 folds or more) as compared to that of the original dispersion, to 1 mg/mL or greater, such as 10 mg/mL or greater. The one or more non-volatile materials in the original continuous phase may be partially or substantially removed during this concentration process, or concomitantly concentrated in the intennediate dispersion as well to a degree similar to that of the bioactive macromolecules and/or the microparticles.

EXAMPLE 1

Antibody microspheres were prepared using an approximately 10 mL aqueous reaction solution (buffered with 0.1 M ammonium acetate, pH 5.8) of about 1 mg/mL antibody (murine monoclonal anti-factor VIII, Baxter Healthcare, Hayward, Calif.) and about 150 mg/mL of an exemplary non-volatile material (a non-ionic polymer, PEG 8000) in a reaction vessel at an elevated temperature of about 50° C. The reaction solution was then cooled at a controlled rate by immersing the reaction vessel containing the reaction solution in an ice bath (about 4° C.) for approximately 30 min. Turbidity developed in the reaction vessel, indicating the formation of a dispersed phase containing antibody microspheres in a continuous phase containing the aqueous solution in which the PEG 1000 was dissolved. A volume (approximately 3 mL) of a non-solvent (PEG 300) having a density greater than that of the continuous phase was placed in a 15 mL conical polypropylene centrifuge tube, and cooled on ice (about 4° C.). Using a pipette, an approximately 1 mL sample of the antibody microsphere suspension was carefully placed in the centrifuge tube, on top of the non-solvent, without substantially mixing the two systems. The centrifuge tube was centrifuged at 3,000×g at about 4° C. for about 30 min to selectively effect migration of the microparticles from the continuous phase into and through the non-solvent. A pellet of the antibody microspheres was observed at the bottom of the centrifuge tube, some microspheres remained in suspension in the non-solvent, and the bulk of the continuous phase remained on top of the non-solvent. The supernatant (containing the bulk of the continuous phase and the non-solvent) was aspirated out of the centrifuge tube, and about 0.2 mL of fresh non-solvent (PEG 300) was added into the centrifuge tube to re-suspend the antibody microspheres. An approximately 20 μL aliquot of the re-suspension was taken for microscopic examination, which showed that most of the microspheres therein appeared as non-agglomerated spherical particles of about 2-3 microns in diameter.

Upon mixing with about 1 mL volume of a physiological solution (PBS), the remaining re-suspension (approximately 180 μL) turned visibly clear within a few seconds, indicating that the antibody microspheres were soluble in the physiological solution. The mixture was dialyzed against the physiological solution to remove the non-solvent (PEG 300) completely, and then analyzed by size exclusion chromatography to assess the molecular integrity of the re-solubilized antibody. The percentage monomer of the re-solubilized antibody was about 98% whereas the starting material had a monomer content of about 98.4%. Accordingly, these results indicate that the antibody molecules were intact and not adversely affected by the microsphere formation or by the non-solvent separation processes.

EXAMPLE 2

Antibody microspheres were prepared using an approximately 5 mL aqueous reaction solution containing about 4.75 mL of a 1 mg/mL antibody (murine monoclonal anti-factor VIII from Baxter Healthcare, Hayward, Calif.) solution in PBS buffer (pH 6) and about 500 mg of an exemplary non-volatile material (a non-ionic polymer, poloxamer 188) in a reaction vessel at an elevated temperature of approximately 50° C. The reaction solution was then cooled at a controlled rate by immersing the reaction vessel containing the reaction solution in an ice bath (about 4° C.) for about 30 min. Turbidity developed in the reaction vessel, indicating the formation of a dispersed phase containing antibody microspheres in a continuous phase containing the aqueous solution in which the poloxamer 188 was dissolved. A volume (1 mL) of a non-solvent (PEG 300) having a density greater than that of the continuous phase was placed in a 15 mL conical polypropylene centrifuge tube, and cooled on ice (about 4° C.). Using a pipette, the antibody microsphere suspension was carefully placed in the centrifuge tube, on top of the non-solvent, without substantially mixing the two systems. The centrifuge tube was centrifuged at 3,000×g at about 4° C. for approximately 30 min to selectively effect migration of the microparticles from the continuous phase into and through the non-solvent. A pellet of the antibody microspheres was observed at the bottom of the centrifuge tube, some microspheres remained in suspension in the non-solvent, and the bulk of the continuous phase remained on top of the non-solvent. A majority (corresponding to approximately top 4 mL) of the supernatant (containing the bulk of the continuous phase) was aspirated out of the centrifuge tube, and the remainder (corresponding to approximately 2 mL of supernatant and the pellet) in the centrifuge tube was repeatedly washed centrifugally with a cold washing medium in which the microspheres were substantially insoluble (acetonitrile at −20° C., 2 mL at a time, centrifuged at 3,000×g at −9° C. for 5 min) to remove the non-solvent and water. Following the last wash, the centrifuge tube was vortexed for 10 seconds to loosen up the pellet, and the residual washing medium therein was removed by solvent evaporation (first under a stream of nitrogen and then under vacuum for 10 min) to form a dry powder of the antibody microspheres.

The dry powder was gently rubbed between two microscope glass slides and examined under a light microscope at 500× magnification. Some of the microspheres appeared segregated (i.e., not in agglomeration), and were about 2-3 microns in diameter. These microspheres were partially soluble in PBS.

EXAMPLE 3

Antibody microspheres were prepared using an approximately 5 mL aqueous reaction solution containing about 4.75 mL of a 1 mg/mL antibody (murine monoclonal anti-factor VIII from Baxter Healthcare, Hayward, Calif.) solution in PBS buffer (pH 6), about 500 mg of an exemplary non-volatile material (a non-ionic polymer, poloxamer 188), and stabilizers (0.1 M histidine and 0.05 M glutamic acid) in a reaction vessel at an elevated temperature of about 50° C. The reaction solution was then cooled at a controlled rate by immersing the reaction vessel containing the reaction solution in an ice bath (about 4° C.) for approximately 30 min. Turbidity developed in the reaction vessel, indicating the formation of a dispersed phase containing antibody microspheres in a continuous phase containing the aqueous solution in which the poloxamer 188 was dissolved. A volume (1 mL) of a non-solvent (PEG 300) having a density greater than that of the continuous phase was placed in a 15 mL conical polypropylene centrifuge tube, and frozen at −20° C. Using a pipette, the 5 mL antibody microsphere suspension was carefully placed in the centrifuge tube, on top of the frozen non-solvent, to ensure substantially no mixing of the two systems took place. The non-solvent was thawed and cooled by placing the centrifuge tube in a water bath at about 37° C. for about 15 min, then in another water bath at about 4° C. for about 30 min, then on ice for about 10 min. The centrifuge tube was centrifuged at 3,000×g at about 4° C. for about 30 min to selectively effect migration of the microparticles from the continuous phase into and through the non-solvent. A pellet of the antibody microspheres was observed at the bottom of the centrifuge tube, some microspheres remained in suspension in the non-solvent, and the bulk of the continuous phase remained on top of the non-solvent. A majority (corresponding to approximately top 4 mL) of the supernatant (containing the bulk of the continuous phase) was aspirated out of the centrifuge tube, and the remainder (corresponding to approximately 2 mL of supernatant and the pellet) in the centrifuge tube was repeatedly washed centrifugally with a cold washing medium (acetonitrile at about −20° C., using about 2 mL at a time, and centrifuged at 3,000×g at about −9° C. for about 5 min) in which the microspheres were substantially insoluble to remove the non-solvent and water. Following the last wash, the centrifuge tube was agitated (vortexing) for about 10 seconds to loosen up the pellet, and the residual washing medium therein was removed by solvent evaporation (first under a stream of nitrogen and then under vacuum for about 10 min) to form a dry powder of the antibody microspheres.

The dry powder was gently rubbed between two microscope glass slides and examined under a light microscope at 500× magnification. Most of the microspheres appeared segregated (i.e., not in agglomeration), and were about 2-3 microns in diameter. These microspheres were readily soluble in PBS.

EXAMPLE 4

An approximately 1 mL aqueous reaction solution was prepared by dissolving a lyophilized concentrate of humanized therapeutic monoclonal antibody Infliximab (Centocor, Malvern, Pa.) in a reconstitution medium at a concentration of about 100 mg/mL, dialyzing the reconstitution against an approximately 0.1 M ammonium acetate buffer (pH 5.9, containing poloxamer 188 at 10% w/v) to achieve an antibody concentration of 1 mg/mL. The reaction solution was placed in a reaction vessel at an elevated temperature of about 45° C. The reaction solution was then cooled at a first controlled rate to about 22° C. over a time period of about 30 min, and then at a second controlled rate to about 4° C. over a time period of about 15 min. Turbidity developed in the reaction vessel, indicating the formation of a dispersed phase containing antibody microspheres in a continuous phase containing the aqueous solution in which the poloxamer 188 was dissolved. A volume (1 mL) of a non-solvent comprising about 60% w/v water, about 25% w/v PEG 300, about 10% w/v ethanol, about 5% w/v poloxamer 188 and having a density greater than that of the continuous phase was placed in a 15 mL conical polypropylene centrifuge tube, and frozen at about −20° C. Using a pipette, the 1 antibody microsphere suspension was carefully placed in the centrifuge tube, on top of the frozen non-solvent, to ensure substantially no mixing of the two systems took place. The non-solvent was thawed and cooled by placing the centrifuge tube in a water bath at approximately 37° C. for about 15 min, then in another water bath at approximately 4° C. for about 30 min, then on ice for about 10 min. The centrifuge tube was centrifuged at 3,000×g at about 4° C. for about 10 min to selectively effect migration of the microparticles from the continuous phase into and through the non-solvent. A pellet of the antibody microspheres was observed at the bottom of the centrifuge tube, some microspheres remained suspended in the non-solvent, and the bulk of the continuous phase remained on top of the non-solvent. A majority (greater than about 1 mL) of the supernatant was aspirated out of the centrifuge tube, and the remainder (less than about 1 mL of non-solvent and the pellet) in the centrifuge tube was suitable for end use (e.g., injection, inhalation) upon re-suspension with agitation because the non-solvent employed in this example was a pharmaceutically acceptable fluid carrier (e.g., diluent).

EXAMPLE 5

An approximately 20 L aqueous reaction solution was prepared by dissolving human immunoglobulin (Bayer Corp., Elkhart, Ind.) at a concentration of about 1 mg/mL in an ammonium acetate buffer (pH 5.8) containing about 12% w/v of a representative non-volatile material (a non-ionic polymer, poloxamer 188). The reaction solution was heated to about 50° C. and then gradually cooled to about 4° C. over approximately 2 hrs to form a dispersed phase containing IVIG microspheres in a continuous phase containing the aqueous solution in which the poloxamer 188 was dissolved. At about 4° C., a volume (approximately 200 mL) of a non-solvent (anhydrous PEG 300) having a density greater than that of the continuous phase of the antibody microsphere dispersion was pumped into the rotor of a continuous-flow centrifuge (Sorvall® Contifuge®, Thermo Fisher Scientific, Waltham, Mass.) while spinning at 20,000×g at about 4° C. The antibody microsphere suspension was pumped into the spinning rotor at a flow rate of about 120 mL/min, followed by a first volume (about 1 L) of a first chaser (deionized water) and a second volume (about 1 L) of a second chaser (anhydrous PEG 300), all at the same flow rate. The chasers were used to wash out excess poloxamer 188 and residual water. The rotor was stopped and emptied of all fluids. The IVIG microspheres, cumulated on the inner wall of the rotor as a viscous paste, and were collected by mechanical means (e.g., scraped off).

An aliquot of the collected antibody microspheres was examined by light microscopy (500× magnification) after being suspended in a volume of anhydrous PEG 300. The IVIG microspheres were found to be mostly discrete microspheres of about 2-3 microns in diameter, with little agglomeration. Addition of PBS produced a visibly clear solution within a few seconds, which indicates that the collected IVIG microspheres were soluble in PBS and do not include any visibly insoluble IVIG aggregates.

EXAMPLE 6

Approximately 20 L of an aqueous reaction solution was prepared by dissolving human immunoglobulin G (IgG) at a concentration of about 1 mg/mL in an ammonium acetate buffer (pH 5.8) containing about 12% w/v poloxamer 188. The reaction solution was heated to about 50° C. and then gradually cooled to about 4° C. over approximately 2 hrs to form a dispersed phase containing IgG microspheres in a continuous phase containing the aqueous solution in which the poloxamer 188 was dissolved. At about 4° C., a volume (about 200 mL) of a non-solvent comprising about 75% w/v deionized water, 25% w/v PEG-3350, 10 mM histidine, 100 mM NaCl, and having a pH of about 7.4 and a density greater than that of the continuous phase was pumped into the rotor of a continuous-flow centrifuge (Sorvall® Contifuge®, Thermo Fisher Scientific, Waltham, Mass.) while spinning at 20,000×g at about 4° C. The antibody microsphere suspension was pumped into the spinning rotor at a flow rate of about 120 mL/min, followed by a fresh volume (about 1 L) of the non-solvent as a chaser to wash out excess poloxamer 188 from the collected microspheres. The rotor was stopped and emptied of all fluids. The IgG microspheres which accumulated on the inner wall of the rotor as a viscous paste, were collected by mechanical means (e.g., scraped off).

An aliquot of the collected antibody microspheres was examined by light microscopy (500× magnification) after being suspended in a fresh volume of the non-solvent. The IgG microspheres were found to be mostly discrete microspheres of about 2-3 microns in diameter, with little agglomeration. The concentration of human IgG in the collected antibody microspheres was determined by diluting an aliquot of the collected microspheres 1000-fold by volume in PBS (completely dissolved the IgG microspheres), and measuring the optical density of the dilution at 280 nm. Based on an extinction coefficient of about 1.38, the IgG concentration in the collected microspheres was determined to be about 298 mg/mL. Comparing this concentration to the 1 mg/mL concentration of IgG in the reaction solution, the process described above concentrated the IgG molecules about 300-fold.

What is claimed is:

1. A method of processing multi-phasic dispersions comprising:

providing a multi-phasic dispersion including dispersed and continuous phases, the dispersion comprising solid microparticles and at least a first non-volatile material;

providing a non-solvent, combining the multi-phasic dispersion and the non-solvent; and selectively effecting migration of the microparticles into or through the non-solvent such that a majority of the microparticles is separated from the dispersion, wherein the continuous phase is either aqueous or aqueous-miscible, the first non-volatile material comprises a non-ionic aqueous-soluble polymer or a non-ionic aqueous-miscible polymer, the microparticles arc substantially insoluble in the non-solvent and the non-solvent has either a density which is greater than that of the continuous phase or a viscosity which is greater than that of the continuous phase, wherein providing the non-solvent comprises introducing the non-solvent into a centrifugation apparatus, thereby forming a non-solvent layer therein, combining the multi-phasic dispersion and the non-solvent comprises layering the multi-phasic dispersion on a top surface of the non-solvent layer, thereby forming a layered composition; and selectively effecting migration of the microparticles into or through the non-solvent comprises centrifuging the layered composition.

2. The method of claim 1, further comprising freezing the non-solvent prior to adding the multi-phasic dispersion to the non-solvent.

3. The method of claim 1, wherein the centrifugation apparatus comprises a centrifuge tube.

4. The method of claim 1, wherein the centrifugation apparatus comprises a continuous-flow centrifuge.

5. The method of claim 1, further comprising collecting the microparticles separated from the dispersion.

6. The method of claim 1, wherein the non-solvent comprises a second non-volatile material.

7. The method of claim 6, further comprising collecting the microparticles separated from the dispersion, and exposing the collected microparticles to a supercritical fluid to remove at least a portion of the second non-volatile material while retaining at least the solid microparticles.

8. The method of claim 1, wherein the non-solvent is a pharmaceutically acceptable diluent.

9. The method of claim 1, wherein the microparticles have a density $D_p$, the continuous phase has a density $D_c$, and the non-solvent is homogeneous having a density $D_n$, such that $D_p \geqq D_n \geqq D_c$.

10. The method of claim 9, wherein $D_n$ is greater than 1 g/cm$^3$.

11. The method of claim 1, wherein the non-solvent comprises a density gradient.

12. The method of claim 1, wherein the non-solvent comprises one or more components selected from the group consisting of aqueous liquids, organic liquids, halogenated liquids, non-volatile materials, and combinations thereof.

13. The method of claim 6, wherein the second non-volatile material is water-soluble, a liquid at ambient temperature, or both.

14. The method of claim 6, wherein the concentration of the second non-volatile material in the non-solvent is greater than the concentration of the first non-volatile material in the dispersion.

15. The method of claim 14, wherein the second non-volatile material is different from and has a lower molecular weight than the first non-volatile material.

16. The method of claim 14, wherein the first and second non-volatile materials are the same.

17. The method of claim 6, wherein the second non-volatile material is selected from liquid polyethylene glycols, liquid poloxamers, and combinations of thereof.

18. The method of claim 6, wherein the first and second non-volatile materials comprise non-ionic polymers independently selected from the group consisting of nonionic polyethers, nonionic copolyethers, nonionic polyesters, nonionic copolyesters, nonionic polyether-polyester copolymers, non-ionic vinyl polymers, non-ionic pyrrolidone-containing polymers, non-ionic polymeric carbohydrates, derivatives and salts of the foregoing materials, and combinations thereof.

19. The method of claim 1, wherein the non-solvent further comprises one or more solutes selected from the group consisting of stabilizers, salts, antioxidants, and combinations thereof.

20. The method of claim 1, wherein the non-solvent is soluble in or miscible with the continuous phase.

21. The method of claim 1, wherein each microparticle comprises at least one bioactive macromolecule that is present at least on an outer surface of the microparticle.

22. The method of claim 21, wherein the at least one bioactive macromolecule is selected from the group consisting of carbohydrates, peptides, proteins, vectors, nucleic acids, complexes thereof, conjugates thereof, and combinations thereof.

23. The method of claim 1, wherein the microparticles are amorphous, spherical, solid, or a combination of two or more thereof.

24. The method of claim 1, wherein the solid microparticles comprise at least one active agent.

25. The method of claim 24, wherein the active agent is selected from the group consisting of bioactive agents, pharmaceutical agents, diagnostic agents, nutritional supplements, and cosmetic agents.

26. The method of claim 24, wherein the active agent is a bioactive agent comprising at least one bioactive macromolecule selected from the group consisting of carbohydrates, peptides, proteins, vectors, nucleic acids, complexes thereof, conjugates thereof, and combinations thereof.

27. The method of claim 24, wherein the active agent is a pharmaceutical agent selected from the group consisting of adjuvants, adrenergic agents, adrenergic blocking agents, adrenocorticoids, adrenolytics, adrenomimetics, alkaloids, alkylating agents, allosteric inhibitors, anabolic steroids, analeptics, analgesics, anesthetics, anorexiants, antacids, anti-allergic agents, antiangiogenesis agents, anti-arrhythmic agents, anti-bacterial agents, antibiotics, antibodies, anticancer agents, anticholinergic agents, anticholinesterases, anticoagulants, anticonvulsants, antidementia agents, antidepressants, antidiabetic agents, antidiarrheals, antidotes, antiepileptics, antifolics, antifungals, antigens, antihelmintics, antihistamines, antihyperlipidemics, antihypertensive agents, anti-infective agents, anti-inflammatory agents, antimalarials, antimetabolites, antimuscarinic agents, antimycobacterial agents, antineoplastic agents, antiosteoporosis agents, antipathogen agents, antiprotozoal agents, adhesion molecules, antipyretics, antirheumatic agents, antiseptics, antithyroid agents, antiulcer agents, antiviral agents, anxiolytic sedatives, astringents, beta-adrenoceptor blocking agents, biocides, blood clotting factors, calcitonin, cardiotonics, chemotherapeutics, cholesterol lowering agents, cofactors, corticosteroids, cough suppressants, cytokines, diuretics, dopaminergics, estrogen receptor modulators, enzymes and cofactors thereof, enzyme inhibitors, growth differentiation factors, growth factors, hematological agents, hematopoietics, hemoglobin modifiers, hemostatics, hormones and hormone analogs, hypnotics, hypotensive diuretics, immunological agents, immunostimulants, immunosuppressants, inhibitors, ligands, lipid regulating agents, lymphokines, muscarinics, muscle relaxants, neural blocking agents, neurotropic agents, paclitaxel and derivative compounds, parasympathomimetics, parathyroid hormone, promoters, prostaglandins, psychotherapeutic agents, psychotropic agents, radio-pharmaceuticals, receptors, sedatives, sex hormones, sterilants, stimulants, thrombopoietics, trophic factors, sympathomimetics, thyroid agents, vaccines, vasodilators, vitamins, xanthines, as well as conjugates, complexes, precursors, metabolites, and mixtures thereof.

28. The method of claim 1, wherein the microparticles comprise a carrier macromolecule.

29. A method of processing multi-phasic dispersions comprising:
providing a multi-phasic dispersion including dispersed and continuous phases, the dispersion comprising solid microparticles and a first non-volatile material at a first concentration, the continuous phase is either aqueous or aqueous-miscible, the first non-volatile material comprises a non-ionic aqueous-soluble polymer or a non-ionic aqueous-miscible polymer;
providing a non-solvent comprising a second non-volatile material at a second concentration that is greater than the first concentration, wherein the microparticles are substantially insoluble in the non-solvent;
combining the multi-phasic dispersion and the non-solvent; and
selectively effecting migration of the microparticles into or through the non-solvent such that a majority of the microparticles is separated from the dispersion,
wherein providing the non-solvent comprises introducing the non-solvent into a centrifugation apparatus, thereby forming a non-solvent layer therein, combining the multi-phasic dispersion and the non-solvent comprises layering the multi-phasic dispersion on a top surface of the non-solvent layer, thereby forming a layered composition; and selectively effecting migration of the microparticles into or through the non-solvent comprises centrifuging the layered composition.

30. The method of claim 29, wherein the microparticles comprise an active agent.

31. The method of claim 29, wherein the microparticles comprise a macromolecule selected from the group consisting of carrier macromolecules, bioactive macromolecules, and combinations thereof.

32. The method of claim 31, wherein the macromolecule comprises at least one bioactive macromolecule selected from the group consisting of carbohydrates, peptides, proteins, vectors, nucleic acids, complexes thereof, conjugates thereof, and combinations thereof.

33. The method of claim 29, wherein the first and second non-volatile materials are different in their chemical structure and/or molecular weight.

34. The method of claim 29, wherein the first and second non-volatile materials are the same.

* * * * *